US007608611B2

(12) United States Patent
Ross et al.

(10) Patent No.: US 7,608,611 B2
(45) Date of Patent: Oct. 27, 2009

(54) HSP90 INHIBITORS, METHODS OF MAKING AND USES THEREFOR

(75) Inventors: David Ross, Boulder, CO (US); David Siegel, Denver, CO (US); Philip Reigan, Denver, CO (US); Wenchang Guo, Denver, CO (US); Daniel L. Gustafson, Denver, CO (US)

(73) Assignee: The Regents of the University of Colorado, Denver, CO (US)

( * ) Notice: Subject to any disclaimer, the term of this patent is extended or adjusted under 35 U.S.C. 154(b) by 130 days.

(21) Appl. No.: 11/218,320

(22) Filed: Aug. 31, 2005

(65) Prior Publication Data

US 2006/0205705 A1    Sep. 14, 2006

Related U.S. Application Data

(60) Provisional application No. 60/660,742, filed on Mar. 11, 2005.

(51) Int. Cl.
| | | |
|---|---|---|
| *A01N 43/00* | (2006.01) | |
| *A61K 31/33* | (2006.01) | |
| *C07D 225/00* | (2006.01) | |
| *C07D 295/00* | (2006.01) | |

(52) U.S. Cl. ...................................... 514/183; 540/450
(58) Field of Classification Search ........................ None
See application file for complete search history.

(56) References Cited

U.S. PATENT DOCUMENTS

| 2,601,994 | A | 7/1952 | Richman |
| 6,015,659 | A | 1/2000 | Welch et al. |
| 6,855,705 | B1 | 2/2005 | Tian et al. |
| 6,872,715 | B2 | 3/2005 | Santi et al. |
| 2005/0054625 | A1 | 3/2005 | Johnson, Jr. et al. |
| 2005/0227955 | A1 | 10/2005 | Adams et al. |
| 2006/0019941 | A1 | 1/2006 | Adams et al. |

FOREIGN PATENT DOCUMENTS

| WO | WO 94/08578 | * | 4/1994 |
| WO | WO 02/079167 | * | 10/2002 |
| WO | WO 03/066005 | | 8/2003 |
| WO | WO2005063714 | * | 7/2005 |
| WO | WO 2005063714 A1 | | 7/2005 |
| WO | WO 2005/095347 | | 10/2005 |
| WO | WO 2005095347 A1 | | 10/2005 |

OTHER PUBLICATIONS

Andrus et al. Journal of Organic Chemistry, 2003, 68, 8162-8169.*
Schnur er al. Journal of Medicinal Chemistry, 1995, 38, 3806-3812.*
Miller et al. Cancer Research, 1994, 2724-2730.*
Ariese et al. Aquatic Sciences, 2004, 66, 86-94.*
Secretary, Codex Alimentarius Commission. Codex alimentarius commission, World Health Organization, Mar. 2002.*
Lucken, E.A.C. The Journal of the Chemical Society, Nov. 1964, 4234-4240.*
Whitesell et al. Proceedings of the National Academy of Sciences, 1994, 91, 8324-8328.*
Ross. Drug Metabolism Reviews, 2004, 36 (3-4), 659-654.*
Andrus et al. Journal of Organic Chemistry, 68(21), 8162-69.*
Berge et al. Journal of Pharmaceutical Sciences, 1977, 66(1), 1-19.*
International Search Report for related PCT application No. PCT/US05/31524.
Written Opinion for related PCT application No. PCT/US05/31524.
Extended European Search Report or Application No. EP 05810418. 3, dated Feb. 16, 2009.
International Search Report for International (PCT) Patent Application No. PCT/US08/74077, mailed Nov. 19, 2008.
Written Opinion for International (PCT) Patent Application No. PCT/US08/74077, mailed Nov. 19, 2008.
Kelland, et al., "DT-Diaphorase expression and tumor cell sensitivity to 17-allylamino, 17-demethoxygeldanamycin, an inhibitor of heat shock protein 90", Journal of the National Cancer Institute, Nov. 17, 1999, vol. 91, No. 22, pp. 1940-1949.
Guo, et al., "Formation of 17-Allyiamino-demethoxygeldanamycln (17-AAG) hydroquinone by NAD (P) H:quinone oxidoreductase 1: role of 17-AAG hydroquinonein heat shock protein 90 inhibition", Cancer Res., Nov. 1, 2005, vol. 65, No. 21, pp. 10006-10015.
Dehn, at al., "Development of a new isogenic cell-xenograft system for evaluation of NAD(P)H:quinone oxidoreductase-directed antitumor quinones: evaluation of the activity of RH1.", Clin. Cancer Res., May 1, 2004, vol. 10, No. 9, pp. 3147-3155.
Guo, et al., "The Bioreduction of a Series of Benzoquinone Ansamycins by NAD(P)H: Quinone Oxidoreductase 1 to more potent heat shock protein 90 inhibitors, the Hydroquinone Ansamycins", Molecular Pharmacology, 2006, vol. 70, No. 4, pp. 1194-1203.
Tziveleka, et al., "Antioxidant Potential of Natural and Synthesised Polyprenylated Hydorquinones", Bioorganic and Medical Chemistry, 2002, vol. 10, pp. 935-939.
Cysyk, et al., "Reaction of Geldanamycin and C17-Substituted Analogues with Gluthathione: Product Indentifications and Pharmacological Implications", Chem Res. Toxicol., 2006, vol. 19, pp. 376-381.
Hu, et al., "Isolation and characterization of novel geldanamycin analogs", Journal of Antibiotics, 2004, vol. 57, No. 7, pp. 421-428.

* cited by examiner

*Primary Examiner*—James O Wilson
*Assistant Examiner*—Noble Jarrell
(74) *Attorney, Agent, or Firm*—Sheridan Ross P.C.

(57) ABSTRACT

The invention provides purified 18,21-didehydro-18,21-dideoxo-18,21-dihydroxy-geldanamycin derivatives, pharmaceutically acceptable salts thereof and prodrugs thereof that are potent Hsp90 binding agents that are useful for the treatment and/or the amelioration of symptoms of cancer and other proliferative tissue disorders.

10 Claims, 7 Drawing Sheets

HSP90 INHIBITORS, METHODS OF MAKING AND USES THEREFOR

CROSS REFERENCE TO RELATED APPLICATIONS

This application claims priority under 35 U.S.C. § 119(e) to U.S. Provisional Patent Application Ser. No. 60/660,742 filed Mar. 11, 2005, which is incorporated herein in its entirety by this reference.

GOVERNMENT INTEREST

This invention was made with government support under National Cancer Institute (NCI) grant CA51210. The government has certain rights in the invention.

FIELD OF THE INVENTION

This invention relates to geldanamycin derivatives as anti-cancer compounds, pharmaceutical compositions containing the same, and methods of using the same in the treatment of neoplastic disorders and solid tumors in a mammal.

BACKGROUND OF THE INVENTION

Hsp90 is a protein chaperone that utilizes the hydrolysis of ATP to assist in the folding of early nascent forms of proteins to their mature, correctly-folded forms. Once the protein has been correctly folded, Hsp90 is released and thus, it functions as a true protein "catalyst." Hsp90 has also been recognized as an attractive anticancer target in that this chaperone assists in the folding of many oncogenic proteins including ErbB2, Raf-1, mutant p53, estrogen and steroid receptors. Thus, by inhibiting Hsp90, a large number of downstream oncogenic proteins can be disrupted, thereby attacking the neoplastic process at a number of points.

The first Hsp90 inhibitor used clinically was geldanamycin. Geldanamycin is a benzoquinone ansamycin polyketide isolated from *Streptomyces geldanus*. Although originally discovered by screening microbial extracts for antibacterial and antiviral activity, geldanamycin was later found to be cytotoxic to tumor cells in vitro and to reverse the neoplastic morphology of cells transformed by the Rous sarcoma virus.

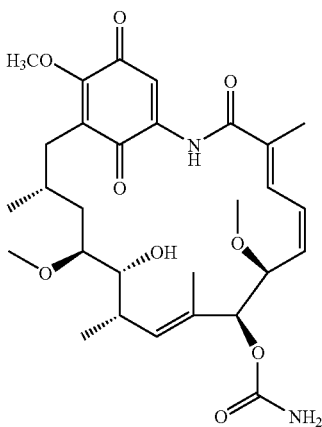

Geldanamycin

Unfortunately, the administration of geldanamycin produced unacceptable hepatotoxicity, which led to its withdrawal from Phase I clinical trials. Second generation geldanamycin derivatives were developed including 17-demethoxy-17-(2-propenylamino)-geldanamycin (17AAG; also known as 17-allylaminogeldanamycin) and 17-demethoxy-17-[[2-(dimethylamino)ethyl]amino]-geldanamycin (17-DMAG). These molecules do not induce liver toxicity and have shown success in Phase I and Phase II clinical trials.

While there has been a great deal of research interest in the benzoquinone ansamycins, particularly geldanamycin and 17-AAG, there remains a need for effective derivatives of these compounds having higher activity without the significant risk of hepatotoxicity of the parent geldanamycin compound.

SUMMARY OF THE INVENTION

The present invention provides novel 18,21-didehydro-18,21-dideoxo-18,21-dihydroxy-geldanamycin derivatives (hydroquinone ansamycins, hereinafter referred to as "18,21-dihydroxy-geldanamycin derivatives"), pharmaceutically acceptable salts thereof or prodrugs thereof that are potent Hsp90 binding agents with surprisingly improved Hsp90 inhibitory and tumor cell toxicity profiles relative to the parent quinones.

One embodiment of the invention is a purified compound having the chemical structure of Formula I:

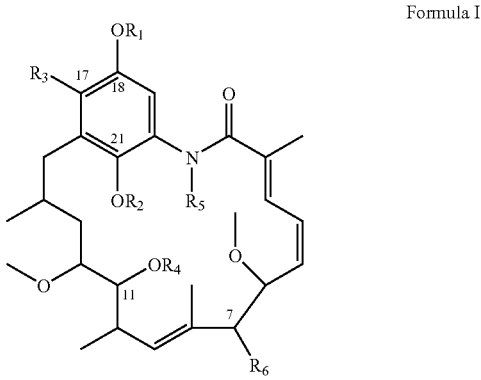

Formula I or a pharmaceutically-acceptable salt thereof;
wherein:

$R_1$ and $R_2$ are independently H, $C_{1-6}$ alkyl $C_{3-8}$ cycloalkyl, $C(=O)C_{1-10}$ alkyl, $C(=O)(CH_2)_n$-cycloalkyl, $C(=O)(CH_2)_n$-aryl, wherein n=1-10, alkoxy, alkylthiol, glycoside, glucuronide or sulfate, $C(=O)CH(X)NH_2$, and $C(=O)CH(X)OH$, wherein X=an amino acid side chain;

$R_3$ is H, $NHCH_2CH=CH_2$, $NHCH_2CH_2N(CH_3)_2$, $NHCH_2CH_2NC_4H_8$, azetidinyl, furfuryl, morpholinyl, piperazinyl, piperidinyl, piperazinyl, pyrrolidinyl, tetrahydrofurfuryl, 2-methyl-1-aziridinyl, (dimethylamino)methyl-1-aziridinyl, 3-(dimethylamino)-1-azetidinyl, 3-hydroxy-1-pyrrolidinyl, 3,4-dihydroxy-1-pyrrolidinyl, or $NR_7R_8$, $OR_7$, $SR_7$, wherein $R_7$ and $R_8$ are independently H, $C_{1-10}$ alkyl, alkenyl, alkynyl, alkoxy, alkylhalide, alkyldihalide, amine, cycloalkyl, carboxyalkyl, (acetylamino)alkyl, (dimethylamino)alkyl, 1-(methoxymethyl)alkyl, 2-(1,3-dioxolan-2-yl)alkyl, 4,4-dimethoxybutyl, [[(1,1-dimethylethoxy)carbonyl]amino]alkyl, [[(1,1-dimethylethoxy)carbonyl]alkylamino]alkyl, 1-(hydroxymethyl)alkyl, 1-(hydroxymethyl)-2-methylalkyl, 2-(hydroxymethyl)cycloalkyl, (diethylamino)alkyl, 2-(dimethylamino)-1-methylethyl, (ethylmethylamino)alkyl, [(2-fluoroethyl)methylamnino]alkyl, [(2,2-difluoroethyl)methylamino]alkyl, [bis(2-hydroxyethyl)amino]alkyl, (dimethyloxidoamino)alkyl, (trimethylammonio)alkyl, (1-aziridinyl)alkyl, (1-aziridinylmethyl)alkyl, (1-azetidinyl)alkyl, (2-deoxy-D-glucos-2-yl), (6-deoxy-D-glucos-6-yl), (1H-imidazol-4-yl)

alkyl, (1-methyl-1H-imidazol-4-yl)alkyl, (1-methyl-1H-imidazol-5-yl)alkyl, (4-morpholinyl)alkyl, (4-pyridinyl)alkyl, (1-piperidinyl)alkyl, (1-piperazinyl)alkyl, (1-pyrrolidinyl)alkyl, (1-ethyl-2-pyrrolidinyl)methyl, or 2-(N-methyl-pyrrolidin-2-yl)ethyl; and wherein when $R_1$ and $R_2$ are both H, $R_3$ is not $OCH_3$ or $NH_2$;

$R_4$ and $R_5$ are independently H, $C_{1-6}$ alkyl, $C_{3-8}$ cycloalkyl, $C(=O)C_{1-10}$ alkyl, $C(=O)(CH_2)_n$-aryl, $C(=O)(CH_2)_n$-cycloalkyl, alkoxy, alkylthiol, glycoside, glucuronide or sulfate, wherein n=1-10; and, $R_6$ is 0, $OC(=O)NH_2$, $OC(=O)C_{1-10}$ alkyl, $OSO_2OH$, $OC(=O)OSO_2OH$ and $OC(=O)NR_9R_{10}$ wherein $R_9$ and $R_{10}$ are independently H and $C_{1-10}$ alkyl.

One specific embodiment of the present invention is a purified compound of Formula I or a pharmaceutically-acceptable salt thereof, wherein:

$R_1$ and $R_2$ are independently H, $C_{1-6}$ alkyl, $C_{3-8}$ cycloalkyl, $C(=O)C_{1-10}$ alkyl, $C(=O)(CH_2)_n$-cycloalkyl, $C(=O)(CH_2)_n$-aryl, wherein n=1-10, alkoxy, alkylthiol, glycoside, glucuronide or sulfate, $C(=O)CH(X)NH_2$, and $C(=O)CH(X)OH$ wherein X=an amino acid side chain;

$R_3$ is H, $NHCH_2CH=CH_2$, $NHCH_2CH_2N(CH_3)_2$, $NHCH_2CH_2NC_4H_8$, azetidinyl, furfuryl, morpholinyl, piperazinyl, piperidinyl, piperazinyl, pyrrolidinyl, tetrahydrofurfuryl, 2-methyl-1-aziridinyl, (dimethylamino)methyl-1-aziridinyl, 3-(dimethylamino)-1-azetidinyl, 3-hydroxy-1-pyrrolidinyl, 3,4-dihydroxy-1-pyrrolidinyl, or $NR_7R_8$, $OR_7$, $SR_7$, wherein $R_7$ and $R_8$ are independently H, $C_{1-10}$ alkyl, alkenyl, alkynyl, alkoxy, alkylhalide, alkyldihalide, amine, cycloalkyl, carboxyalkyl, (acetylamino)alkyl, (dimethylamino)alkyl, 1-(methoxymethyl)alkyl, 2-(1,3-dioxolan-2-yl)alkyl, 4,4-dimethoxybutyl, [[(1,1-dimethylethoxy)carbonyl]amino]alkyl, [[(1,1-dimethylethoxy)carbonyl]alkylamino]alkyl, 1-(hydroxymethyl)alkyl, 1-(hydroxymethyl)-2-methylalkyl, 2-(hydroxymethyl)cycloalkyl, (diethylamino)alkyl, 2-(dimethylamino)-1-methylethyl, (ethylmethylamino)alkyl, [(2-fluoroethyl)methylamino]alkyl, [(2,2-difluoroethyl)methylamino]alkyl, [bis(2-hydroxyethyl)amino]alkyl, (dimethyloxidoamino)alkyl, (trimethylammonio)alkyl, (1-aziridinyl)alkyl, (1-aziridinylmethyl)alkyl, (1-azetidinyl)alkyl, (2-deoxy-D-glucos-2-yl), (6-deoxy-D-glucos-6-yl), (1H-imidazol-4-yl)alkyl, (1-methyl-1H-imidazol-4-yl)alkyl, (1-methyl-1H-imidazol-5-yl)alkyl, (4-morpholinyl)alkyl, (4-pyridinyl)alkyl, (1-piperidinyl)alkyl, (1-piperazinyl)alkyl, (1-$C_{3-8}$ cycloalkyl, $C(=O)C_{1-10}$ alkyl, $C(=O)(CH_2)_n$-aryl, $C(=O)(CH_2)_n$-cycloalkyl, alkoxy pyrrolidinyl)alkyl, (1-ethyl-2-pyrrolidinyl)methyl, or 2-(N-methyl-pyrrolidin-2-yl)ethyl; and wherein $R_3$ is not $OCH_3$;

$R_4$ and $R_5$ are independently H, $C_{1-6}$ alkyl, alkylthiol glycoside, glucuronide or sulfate, wherein n =1-10; and, $R_6$ is O, $OC(=O)NH_2$, $OC(=O)C_{1-10}$ alkyl, $OSO_2OH$, $OC(=O)OSO_2OH$ and $OC(=O)NR_9R_{10}$ wherein $R_9$ and $R_{10}$ are independently H and $C_{1-10}$ alkyl.

A preferred embodiment of the present invention is a compound of Formula I, wherein:

$R_1$ and $R_2$ are independently H or $C(=O)C_{1-10}$ alkyl;

$R_3$ is $NHCH_2CH=CH_2$, $NHCH_2CH_2N(CH_3)_2$, or $NHCH_2CH_2NC_4H_8$;

$R_4$ and $R_5$ are H, $C_{1-6}$ alkyl, $C_{3-8}$ cycloalkyl, $C(=O)C_{1-10}$ alkyl, $C(=O)(CH_2)_n$-aryl, $C(=O)(CH_2)_n$-cycloalkyl, alkoxy, alkylthiol or sulfate, wherein n=1-10; and, $R_6$ is O, $OC(=O)NH_2$, $OC(=O)C_{1-10}$ alkyl, $OSO_2OH$, $OC(=O)OSO_2OH$ and $OC(=O)NR_9R_{10}$ wherein $R_9$ and $R_{10}$ are independently H and $C_{1-10}$ alkyl.

Another preferred embodiment of the present invention is a compound of Formula I, wherein:

$R_1$ and $R_2$ are independently H or $SO_2OR_{10}$ wherein $R_{10}$ is H or $C_{1-10}$ alkyl.

$R_3$ is $NHCH_2CH=CH_2$, $NHCH_2CH_2N(CH_3)_2$, or $NHCH_2CH_2NC_4H_8$;

$R_4$ and $R_5$ are H, $C_{1-6}$ alkyl, $C_{3-8}$ cycloalkyl, $C(=O)C_{1-10}$ alkyl, $C(=O)(CH_2)_n$-aryl, $C(=O)(CH_2)_n$-cycloalkyl, alkoxy, alkylthiol, glycoside, glucuronide or sulfate, wherein n=1-10; and, $R_6$ is O, $OC(=O)NH_2$, $OC(=O)C_{1-10}$ alkyl, $OSO_2OH$, $OC(=O)OSO_2OH$ and $OC(=O)NR_9R_{10}$ wherein $R_9$ and $R_{10}$ are independently H and $C_{1-10}$ alkyl.

Another preferred embodiment of the present invention is a purified compound having the absolute stereochemistry shown in the chemical structure of Formula II:

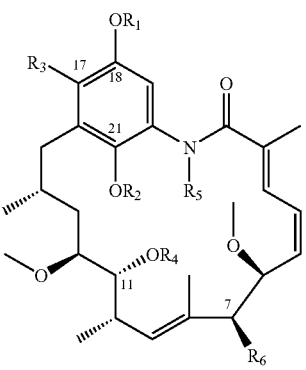

Formula II or a pharmaceutically acceptable salt thereof, wherein the $R_{1-6}$ substituents are as defined above.

One specific embodiment of the invention is a compound having one of the following chemical formulae:

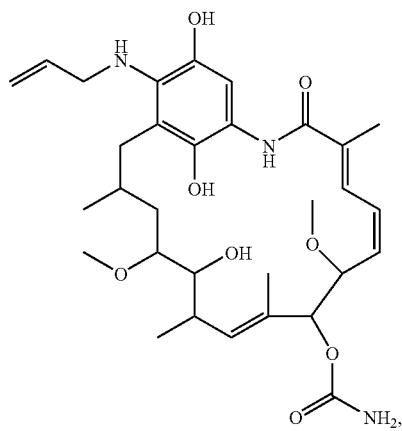

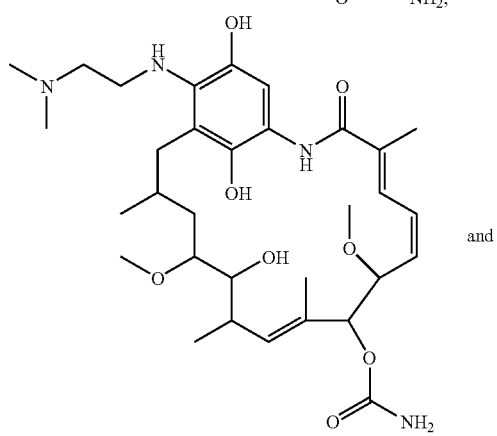

and

-continued

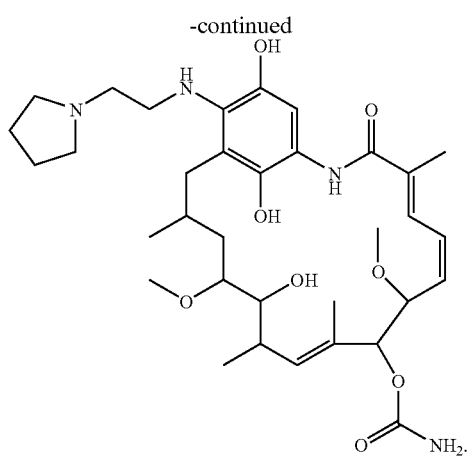

One embodiment of this invention is a method of treating cancer or other proliferative diseases or ameliorating the symptoms of these diseases by administering a therapeutically effective amount of one of these compounds or a pharmaceutically acceptable salt form thereof or prodrugs thereof.

Another embodiment of this invention is a method of treating cancer or other proliferative diseases, or ameliorating a symptom thereof, by administering a therapeutically effective combination of one of the compounds of the present invention and one or more other known anti-cancer or anti-proliferative compounds. For example, the other anti-cancer compounds include at least one of a tyrosine kinase inhibitor, paclitaxel and doxorubicin.

Another embodiment of this invention is a method of treating cancer or other proliferative diseases, or ameliorating a symptom thereof, by administering a therapeutically effective amount of one of the compounds of the present invention in conjunction with medically supervised radiation therapy.

Another embodiment of the present invention is a method of inhibiting the Hsp90 activity in a cell by contacting the cell with one or more of the compounds of the present invention.

Another embodiment of the present invention is a method of disrupting the folding of a protein such as, but not limited to, ErbB2, Raf-1, mutant p53, estrogen and steroid receptors in a cell by contacting the cell with one or more of the compounds of the present invention.

Another embodiment of the present invention is a method of increasing Hsp70 expression in a cell by contacting the cell with one or more of the compounds of the present invention.

Another embodiment of the present invention is a method of increasing Raf-1 degradation in a cell by contacting the cell with one or more of the compounds of the present invention.

Another embodiment of the present invention is a method of decreasing MEK and/or ERK phosphorylation in a cell by contacting the cell with one or more of the compounds of the present invention.

Another embodiment of this invention is a method of testing the susceptibility of a mammal to treatment with one of the compounds of the present invention by testing the mammal for the presence of a mutation in the NQO1 gene in the mammal wherein the presence of a mutation in the NQO1 gene is indicative of limited or no susceptibility to response to a compound of the present invention by the mammal.

Another embodiment of this invention is a method of testing the susceptibility of a mammal to treatment with one of the compounds of the present invention by testing the mammal for the presence NQO1 enzymatic activity in the mammal, wherein reduced or absent NQO1 enzymatic activity is indicative of limited or no susceptibility to response to a compound of the present invention by the mammal.

Another embodiment of this invention is a method of treating cancer or other proliferative disease in a mammal by administering a therapeutically-effective amount of at least one of the compounds:

17-Demethoxy-18,21-dihydroxy-17-(2-propenylamino)-geldanamycin 18-(Acetyloxy)-17-demethoxy-21-hydroxy-17-(2-propenylamino)-geldanamycin 21-(Acetyloxy)-17-demethoxy-18-hydroxy-17-(2-propenylamino)-geldanamycin 18,21-Bis(acetyloxy)-17-demethoxy-21-hydroxy-17-(2-propenylamino)-geldanamycin 17-Demethoxy-18-hydroxy-17-(2-propenylamino)-21-(sulfate)-geldanamycin 17-Demethoxy-21-hydroxy-17-(2-propenylamino)-18-(sulfate)-geldanamycin 18,21-Bis(sulfate)-17-Demethoxy-17-(2-propenylamino)-geldanamycin 17-Amino-17-demethoxy-18,21-dihydroxy-geldanamycin 18-(Acetyloxy)-17-amino-17-demethoxy-21-hydroxy-geldanamycin 21-(Acetyloxy)-17-amino-17-demethoxy-18-hydroxy-geldanamycin 17-Amino-18,21-bis(acetyloxy)-17-demethoxy-21-hydroxy-geldanamycin 17-Amino-17-demethoxy-18-hydroxy-21-(sulfate)-geldanamycin 17-Amino-17-demethoxy-21-hydroxy-18-(sulfate)-geldanamycin 17-Amino-18,21-bis(sulfate)-17-demethoxy-geldanamycin 17-Demethoxy-18,21-dihydroxy-17-[[2-(dimethylamino)ethyl]amino]-geldanamycin 18-(Acetyloxy)-17-demethoxy-17-[[2-(dimethylamino)ethyl]amino]-21-hydroxy-geldanamycin 21-(Acetyloxy)-17-demethoxy-17-[[2-(dimethylamino)ethyl]amino]-18-hydroxy-geldanamycin 18,21-Bis(acetyloxy)-17-demethoxy-17-[[2-(dimethylamino)ethyl]amino]-21-hydroxy-geldanamycin 17-Demethoxy-17-[[2-(dimethylamino)ethyl]amino]-18-hydroxy-21-(sulfate)-geldanamycin 17-Demethoxy-17-[[2-(dimethylamino)ethyl]amino]-21-hydroxy-18-(sulfate)-geldanamycin 18,21-Bis(sulfate)-17-demethoxy-17-[[2-(dimethylamino)ethyl]amino]-geldanamycin 17-Demethoxy-18,21-dihydroxy-17-[[2-(pyrrolidin-1-yl)ethyl]amino-geldanamycin 18-(Acetyloxy)-17-demethoxy-21-hydroxy-17-[[2-(pyrrolidin-1-yl)ethyl]amino-geldanamycin 21-(Acetyloxy)-17-demethoxy-18-hydroxy-17-[[2-(pyrrolidin-1-yl)ethyl]amino-geldanamycin 18,21 Bis(acetyloxy)-17-demethoxy-17-[[2-(pyrrolidin-1-yl)ethyl]amino-geldanamycin 17-Demethoxy-18-hydroxy-17-[[2-(pyrrolidin-1-yl)ethyl]amino-21-(sulfate)-geldanamycin 17-Demethoxy-21-hydroxy-17-[[2-(pyrrolidin-1-yl)ethyl]amino-18-(sulfate)-geldanamycin 18,21-Bis(sulfate)-17-demethoxy-17-[[2-(pyrrolidin-1-yl)ethyl]amino-geldanamycin Additional embodiments of the present invention include the use of metal chelating agents to prevent or reduce the autoxidation of the hydroquinone ansamycin derivatives of the present invention to the corresponding quinione compounds during storage or administration. Additionally, the invention provides pharmaceutical compositions containing hydroquinone ansamycin derivatives and a metal chelating agent.

DETAILED DESCRIPTION OF THE INVENTION

Figure 1:
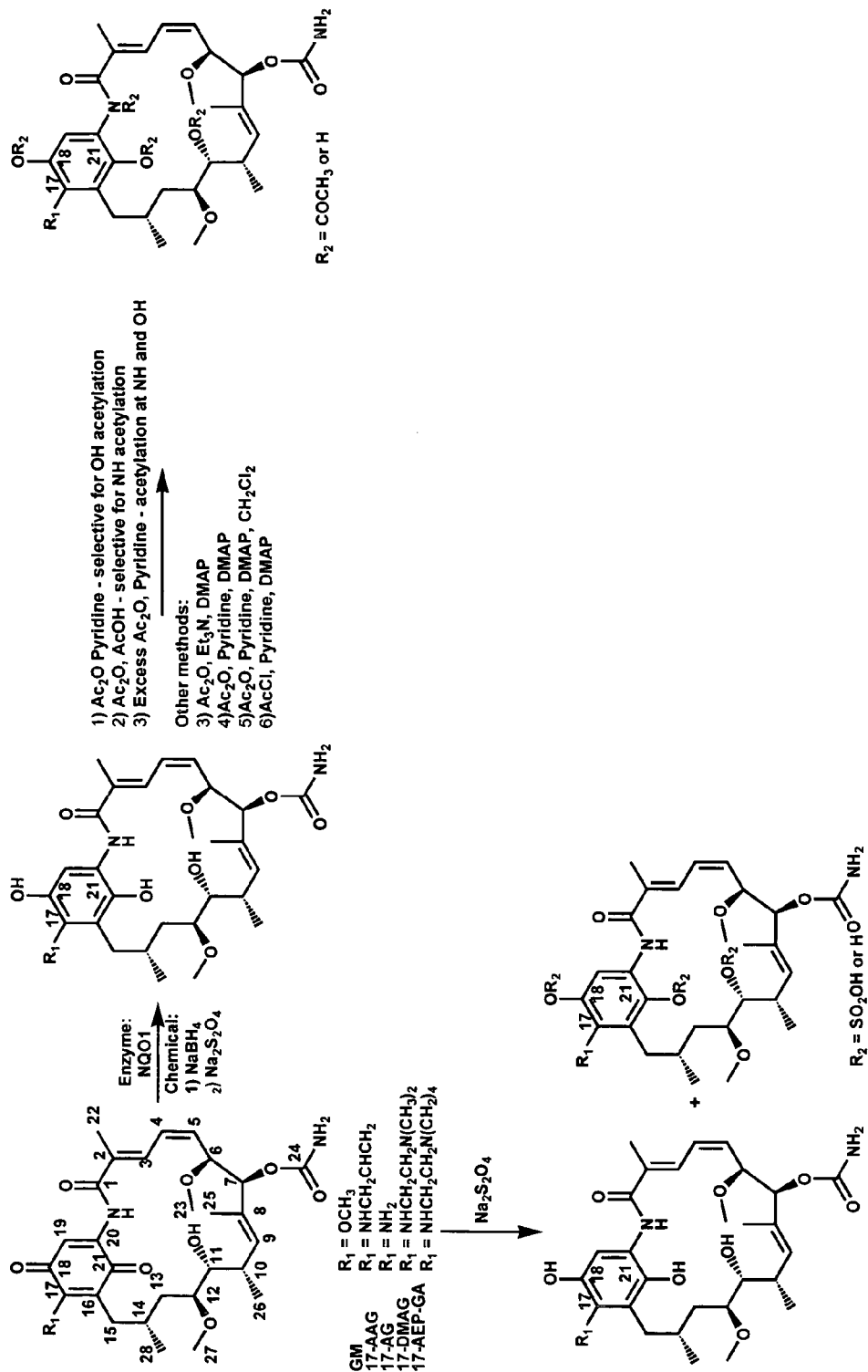
FIG. 1 shows synthetic schemes for the compounds of the present invention.
Figure 2B:
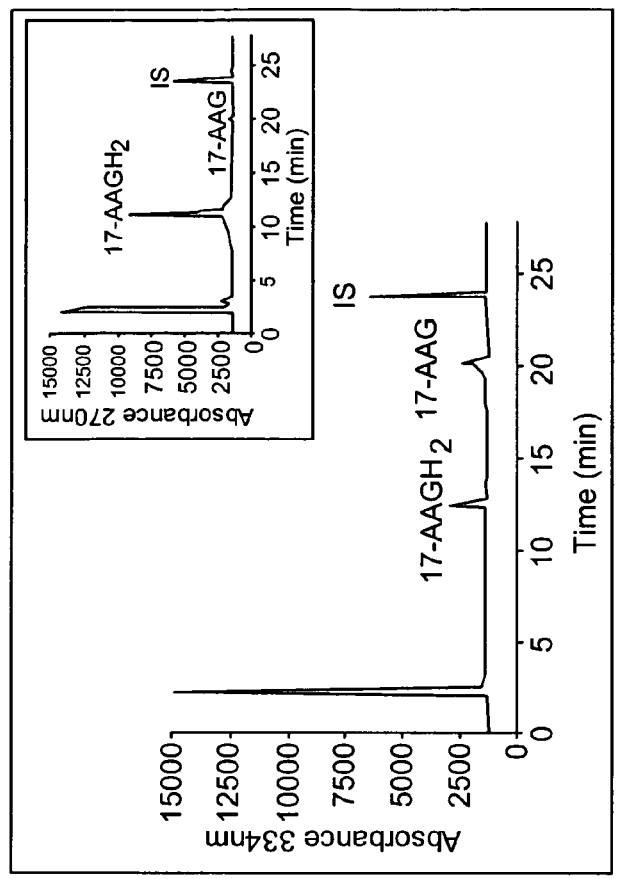
FIG. 2 shows the results of HPLC and LC-MS analysis of the reduction of 17-AAG by NQO1. HPLC analysis confirmed the formation of 17-AAGH$_2$ following reduction of 17-AAG by rhNQO1 (panels A and B) and inhibition of this reduction by the mechanism based inhibitor, ES936. (panel C). Reaction conditions: 50 μM 17-AAG, 200 μM NADH and 3.3 μg rhNQO1 in 50 mM potassium phosphate buffer, pH 7.4 (1 ml) containing 1 mg/ml BSA. After 40 min reactions were stopped with an equal volume of acetonitrile containing internal standard N-phenyl-1-naphthylamine (5 μg/ml), centrifuged and the supernatant was analyzed immediately by HPLC at 334 nm. Panel A, 17-AAG and NADH; panel B, 17-AAG, NADH and rhNQO1; panel C, 17-AAG, NADH, rhNQO1 and ES936 (1 μM). The relatively small peak size of 17-AAGH$_2$ compared to 17-AAG is due to low absorption at 334 nm for the hydroquinone. The inset shows NQO1-mediated metabolism of 17-AAG (same conditions as in panel B) at a detection wavelength of 270 nm where the 17-AAG quinone and hydroquinone have approximately equal absorption. LC/MS was used to confirm 17-AAGH$_2$ as the product of NQO1-mediated reduction of 17-AAG (panel D).
Figure 2A:
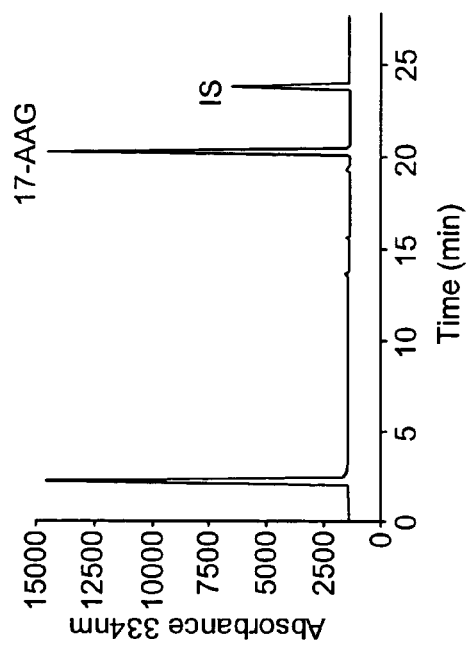
Figure 2C:
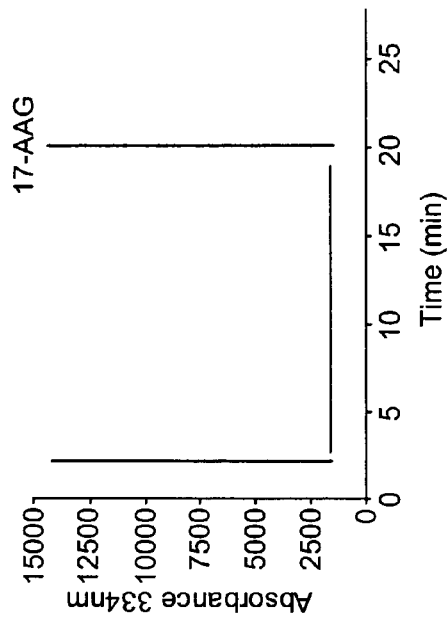
Figure 2D:
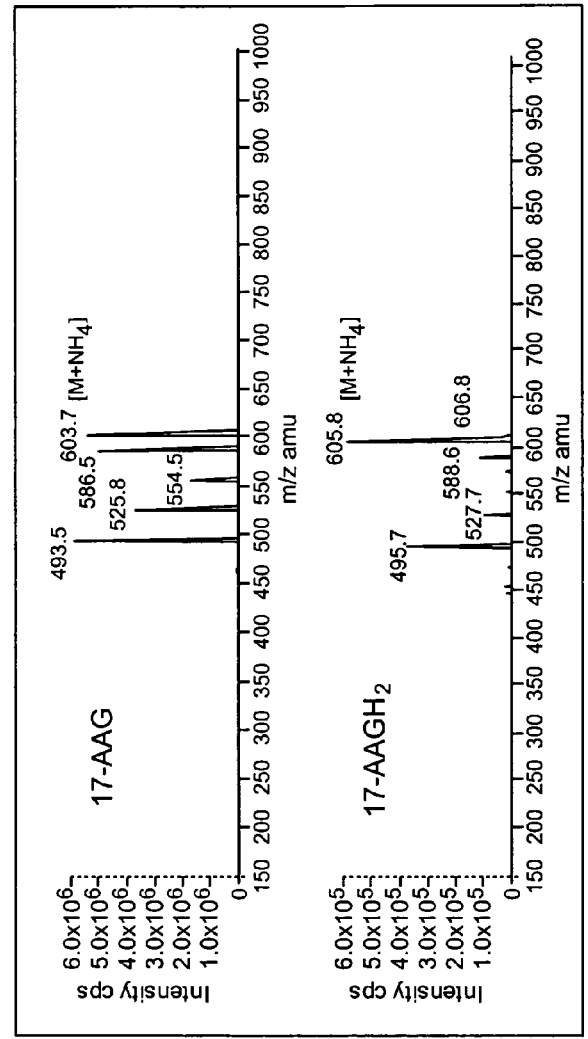

The present invention is drawn to methods of treating cancer or other proliferative diseases in a mammal by the administration of a therapeutically-effective amount of novel 18,21-dihydroxy-geldanamycin derivatives, pharmaceutically-acceptable salts and/or prodrugs thereof to the mammal. Additionally, the invention provides novel 18,21-dihydroxy-geldanamycin derivatives, pharmaceutically-acceptable salts and/or prodrugs thereof for use in pharmaceutical compositions to be administered to a mammal.

The term "alkyl" as used herein is directed to a saturated hydrocarbon group (designated by the formula $C_nH_{2n+1}$) which is straight-chained, branched or cyclized ("cycloalkyl") and which is unsubstituted or substituted, i.e., has had one or more of its hydrogens replaced by another atom or molecule.

"Aryl" designates either the 6-carbon benzene ring or the condensed 6-carbon rings of other aromatic derivatives (see, e.g., Hawley's Condensed Chemical Dictionary (13 ed.), R. J. Lewis, ed., J. Wiley & Sons, Inc., New York (1997)). Aryl groups include, without limitation, phenyl, naphthyl, indanyl and indenyl.

The "aralkyl" group refers to an alkyl group having 1 to 10 carbon atoms substituted with an aryl group "Alkenyl" as used herein by itself or as part of another group refers to straight or branched chain substituent of 2 to 12 carbons, preferably 2 to 5 carbons, in the normal chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, and the like, which may be substituted in the same manner as that described for alkyl groups.

The term "cycloalkyl" as employed herein alone or as part of another group includes saturated cyclic hydrocarbon groups or partially unsaturated (containing 1 or 2 double bonds) cyclic hydrocarbon groups, containing one ring and a total of 3 to 7 carbons, preferably 3 to 6 carbons, forming the ring, which includes cyclopropyl, cyclobutyl, cyclopentyl, cyclohexyl, cycloheptyl, cyclopentenyl and cyclohexenyl, which may be substituted in the same manner as that described for alkyl groups.

"Alkoxy" means —OR where R is alkyl as defined above, e.g., methoxy, ethoxy, propoxy, 2-propoxy, acetyl and the like.

"Alkylthiol" means —SR where R is alkyl as defined above.

"Alkylhalide" designates an alkyl group, as defined above, substituted with one or more halides (F, Cl, Br, I).

"Alkynyl" means a linear monovalent hydrocarbon of two to six carbon atoms or a branched divalent hydrocarbon of three to six carbon atoms, containing at least one triple bond, e.g., ethynyl, propynyl, and the like.

The term "heteroaryl" refers to monocyclic or polycyclic groups having at least one aromatic ring structure and including one or more heteroatoms and preferably one to fourteen carbon atoms. Illustrative examples of heteroaryl groups include, but are not limited to, furanyl, imidazolyl, indanyl, indolyl, indazolyl, isoxazolyl, isoquinolyl, oxazolyl, oxadiazolyl, pyrazinyl, pyridyl, pyrimidinyl, pyrrolyl, pyrazolyl, quinolyl, quinoxalyl, tetrazolyl, thiazolyl, thienyl, and the like.

The term "amino acid side chain" refers to the side chain of any of the known alpha-amino acids such as the side chain of arginine, histidine, alanine, glycine, lysine, glutamine, leucine, valine, serine, homoserine, allothreonine, naphthylalanine, isoleucine, phenylalanine and the like. In instances in which a compound is synthesized or derivatized to include an amino acid side chain, the side chain used is preferably chosen from the side chains of the naturally-occurring amino acids.

The term "glycoside" refers to any compound that contains a carbohydrate molecule (sugar), bonded through its anomeric carbon to a non-sugar group by either an oxygen or a nitrogen atom.

The term "glucuronide" as used herein refers to the compound or metabolite that results from the reaction of glucuronic acid with an acid or alcohol or phenol moiety on the parent compound to form a covalent link between the parent compound and the glucuronic acid through a glycosidic bond.

Substituent groupings, e.g., $C_{1-4}$ alkyl, are known, and are hereby stated, to include each of their individual substituent members, e.g., $C_1$ alkyl, $C_2$ alkyl, $C_3$ alkyl and $C_4$ alkyl.

"Substituted" means that one or more hydrogen atoms on the designated atom is replaced with a selection from the indicated group, provided that the designated atom's normal valency is not exceeded, and that the substitution results in a stable compound.

"Unsubstituted" atoms bear all of the hydrogen atoms dictated by their valency. When a substituent is keto, then two hydrogens on the atom are replaced. Combinations of substituents and/or variables are permissible only if such combinations result in stable compounds; by "stable compound" or "stable structure" is meant a compound that is sufficiently robust to survive isolation to a useful degree of purity from a reaction mixture, and formulation into an efficacious therapeutic agent.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication commensurate with a reasonable benefit/risk ratio.

"Pharmaceutically-acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines, or alkali or organic salts of acidic residues such as carboxylic acids. Pharmaceutically-acceptable salts include the conventional non-toxic salts or the quaternary ammonium salts of the parent compound formed, for example, from non-toxic inorganic or organic acids. Such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. Pharmaceutically acceptable salts are those forms of compounds, suitable for use in contact with the tissues of human beings and animals without excessive toxicity, irritation, allergic response, or other problem or complication, commensurate with a reasonable benefit/risk ratio.

Pharmaceutically-acceptable salt forms of compounds provided herein are synthesized from the parent compound which contains a basic or acidic moiety by conventional chemical methods. Generally, such salts are, for example, prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418, the disclosure of which is hereby incorporated by reference.

"Prodrugs" are intended to include any covalently bonded carriers that release an active parent drug of the present invention in vivo when such prodrug is administered to a mammalian subject. Since prodrugs are known to enhance numerous desirable qualities of pharmaceuticals (i.e., solubility, bioavailability, manufacturing, etc.) the compounds of the present invention may be delivered in prodrug form. Thus, the present invention is intended to cover prodrugs of the presently claimed compounds, methods of delivering the same, and compositions containing the same. Prodrugs of the present invention are prepared by modifying functional groups present in the compound in such a way that the modifications are cleaved, either in routine manipulation or in vivo, to the parent compound. Prodrugs include compounds of the present invention wherein a acyl, hydroxy, amino, or sulfhydryl group is bonded to any group that, when the prodrug of the present invention is administered to a mammalian subject, is cleaved to form a free acetyl, hydroxyl, free amino, or free sulfydryl group, respectively. Examples of prodrugs include, but are not limited to, acetate, formate, and benzoate derivatives of alcohol and amine functional groups in the compounds of the present invention.

The term "therapeutically-effective amount" of a compound of this invention means an amount effective to antagonize abnormal level of CRF or treat the symptoms of affective disorder, anxiety or depression in a host.

As used herein, the term "anti-cancer" or "anti-proliferative" agent includes, but is not limited to, tyrosine kinase inhibitors, paclitaxel and doxorubicin.

It will be appreciated by those skilled in the art that compounds of the invention having a chiral center may exist in, and may be isolated in, optically active and racemic forms. It is to be understood that the compounds of the present invention encompasses any racemic, optically-active, regioisomeric or stereoisomeric form, or mixtures thereof, which possess the therapeutically useful properties described herein. It is well known in the art how to prepare optically active forms (for example, by resolution of the racemic form by recrystallization techniques, by synthesis from optically-active starting materials, by chiral synthesis, or by chromatographic separation using a chiral stationary phase). It is also to be understood that the scope of this invention encompasses not only the various isomers, which may exist but also the various mixtures of isomers, which may be formed. For example, if the compound of the present invention contains one or more chiral centers, the compound can be synthesized enantioselectively or a mixture of enantiomers and/or diastereomers can be prepared and separated. The resolution of the compounds of the present invention, their starting materials and/or the intermediates may be carried out by known procedures, e.g., as described in the four volume compendium Optical Resolution Procedures for Chemical Compounds: Optical Resolution Information Center, Manhattan College, Riverdale, N.Y., and in Enantiomers, Racemates and Resolutions, Jean Jacques, Andre Collet and Samuel H. Wilen; John Wiley & Sons, Inc., New York, 1981, which is incorporated in its entirety by this reference. Basically, the resolution of the compounds is based on the differences in the physical properties of diastereomers by attachment, either chemically or enzymatically, of an enantiomerically pure moiety resulting in forms that are separable by fractional crystallization, distillation or chromatography.

Because 17-AAG, 17-DMAG and related benzoquinone ansamycins contain a quinone moiety, bioreduction of these compounds to form semiquinone and hydroquinone species is a possible metabolic pathway in tumor cells in the presence of the appropriate bioreductive enzymes. NQO1 (DT-diaphorase, EC 1.6.99.2) is a flavoenzyme capable of utilizing either NADH of NADPH as reducing cofactors to catalyze the direct two-electron reduction of quinones to hydroquinones. Thus, amongst the bioreductive enzymes expressed in cancer cells, NQO1 is poised to have the greatest influence on the metabolism of the benzoquinone ansamycins.

NQO1 is expressed at high levels in many human cancers including lung, colon, stomach, pancreatic and breast cancers and has been shown to increase the cytotoxicity of many quinone containing antitumor drugs such as AZQ, mitomycin C, EO9, streptonigrin, RH-1 and β-lapachone by reduction of these compounds to the corresponding hydroquinone species. Kelland et al. (*J. Natl. Cancer Inst.* 1999; 91:1940-49) demonstrated a positive correlation between 17-AAG sensitivity and NQO1 expression. 17-AAG undergoes NQO1-mediated reduction in vitro and human cancer cell lines expressing NQO1 are more sensitive to 17-AAG. The present inventors have discovered that 17-AAG can be reduced to 17-AAGH$_2$ by NQO1. Additionally, studies with purified yeast and human Hsp90 demonstrate that 17-AAGH$_2$ is a more potent inhibitor of Hsp90 than 17-AAG, and molecular modeling studies confirm that 17-AAGH$_2$ has a greater affinity for the ATP binding site in yeast and human Hsp90 than does 17-AAG.

The compounds of the present invention may be prepared in a number of ways well known to one skilled in the art of organic synthesis. The compounds of the present invention can be synthesized using the methods described below, together with synthetic methods known in the art of organic chemistry, or variations thereon as appreciated by those skilled in the art. Preferred methods include, but are not limited to, those described below.

The compounds of this invention may be prepared using the reactions and techniques in this section. The reactions are performed in solvents appropriate to the reagents and materials employed and suitable for the transformation being effected. Also, in the description of the synthetic methods described below, it is to be understood that all proposed reaction conditions, including choice of solvents, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents, which are compatible with the reaction conditions will be readily apparent to one skilled in the art and alternate methods must then be used.

FIG. 1 shows the synthetic scheme for the synthesis of the compounds of the present invention. The benzoquinone ansamycin starting compound is available commercially from Invivogen. This compound can be enzymatically reduced by purified NQO1, as described below, to form the corresponding hydroquinone. Preferably, the compound is enzymatically reduced using purified, recombinant NQO1.

Alternatively, the starting benzoquinone can be reduced chemically using sodium dithionite or sodium borohydride to form the hydroquinone and semiquinone in combination with the corresponding sulfate derivatives at the R$_2$ position. These compounds are then separated and the derivative of interest is recovered.

The hydroquinone formed by chemical or enzymatic reduction of the parent benzoquinone can then be acetylated and modified at position R$_1$ as shown in FIG. 1 to form the ansamycin derivatives of the present invention.

Therefore, one embodiment of the present invention is a method of forming an 18,21-dihydroxy geldanamycin compound or a derivative thereof comprising contacting a geldanamycin benzoquinone with an enzyme under reaction conditions suitable to sustain enzymatic activity of an enzyme capable of reducing the benzoquinone to the semiquinone or to the hydroquinone. In a preferred embodiment, the enzyme is NQO1.

Also provided herein are pharmaceutical-compositions containing compounds of this invention and a pharmaceutically-acceptable carrier, which are media generally accepted in the art for the delivery of biologically active agents to animals, in particular, mammals. Pharmaceutically-acceptable carriers are formulated according to a number of factors well within the purview of those of ordinary skill in the art to determine and accommodate. These include, without limitation: the type and nature of the active agent being formulated; the subject to which the agent-containing composition is to be administered; the intended route of administration of the composition; and, the therapeutic indication being targeted. Pharmaceutically-acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, well known to those of ordinary skill in the art. Descriptions of suitable pharmaceutically-acceptable carriers, and factors involved in their selection, are found in a variety of readily available sources, e.g., Remington's Pharmaceutical Sciences, 17th ed., Mack Publishing Company, Easton, Pa., 1985, the contents of which are incorporated herein by this reference.

Figure 3:
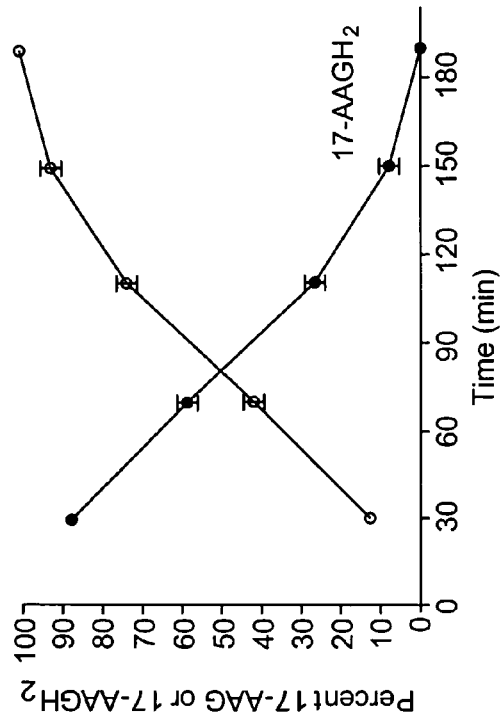
FIG. 3 shows the stability of 17-AAGH$_2$ by examination of the autoxidation of 17-AAGH$_2$ to 17-AAG over time by HPLC. Reaction conditions: 50 μM quinone, 50 μM NADH and 3.3 μg rhNQO1 in 50 mM potassium phosphate buffer, pH 7.4 containing 1 mg/ml BSA, total volume 1 ml at 27° C. Reactions were stopped with an equal volume of acetonitrile containing internal standard and samples were analyzed immediately by HPLC at 270 nm. Results are mean, standard deviation, n=3.

The hydroquinone ansamycin derivatives of the present invention are relatively stable, undergoing autoxidation to the corresponding quinione compound over time (see FIG. 3, and Example 1, below). This autoxidation occurs more rapidly in the presence of metal salts, and particularly in the presence of copper. Therefore, metal chelating agents can be used to prevent the autoxidation of the hydroquinone derivatives of the present invention. Thus, one embodiment of the present invention is a method of reducing the autoxidation of a hydroquinone ansamycin derivative by storing the hydroquinone ansamycin derivative in the presence of a metal chelating agent. A related embodiment is a method of reducing the autoxidation of a hydroquinone ansamycin derivative by administering a therapeutically effective amount of a hydroquinone ansamycin derivative to a mammal in the presence of a metal chelating agent. A further embodiment of the invention is a pharmaceutical composition containing at least one of the ansamycin derivatives of the present invention and a metal chelating agent. Exemplary metal chelating agent suitable for use in the methods and compositions of the present invention include D-penicillamine.

This invention further provides a method of treating a mammal afflicted with a cancer or proliferative disorder, which includes administering to the mammal a pharmaceutical composition provided herein. Such compositions generally comprise a therapeutically effective amount of a compound provided herein, that is, an amount effective to ameliorate, lessen, inhibit or destroy neoplastic tissue. Such amounts typically comprise from about 0.1 to about 1000 mg of the compound per kilogram of body weight of the mammal to which the composition is administered. Therapeutically effective amounts can be administered according to any dosing regimen satisfactory to those of ordinary skill in the art.

Administration is, for example, by various parenteral means. Pharmaceutical compositions suitable for parenteral administration include various aqueous media such as aqueous dextrose and saline solutions; glycol solutions are also useful carriers, and preferably contain a water soluble salt of the active ingredient, suitable stabilizing agents, and if necessary, buffering agents. Antioxidizing agents, such as sodium bisulfite, sodium sulfite, or ascorbic acid, either alone or in combination, are suitable stabilizing agents; also used are citric acid and its salts, and EDTA. In addition, parenteral solutions can contain preservatives such as benzalkonium chloride, methyl- or propyl-paraben, and chlorobutanol.

Alternatively, compositions can be administered orally in solid dosage forms, such as capsules, tablets and powders; or in liquid forms such as elixirs, syrups, and/or suspensions. Gelatin capsules can be used to contain the active ingredient and a suitable carrier such as, but not limited to, lactose, starch, magnesium stearate, stearic acid, or cellulose derivatives. Similar diluents can be used to make compressed tablets. Both tablets and capsules can be manufactured as sustained release products to provide for continuous release of medication over a period of time. Compressed tablets can be sugar-coated or film-coated to mask any unpleasant taste, or used to protect the active ingredients from the atmosphere, or to allow selective disintegration of the tablet in the gastrointestinal tract.

Additional objects, advantages, and novel features of this invention will become apparent to those skilled in the art upon examination of the following examples thereof, which are not intended to be limiting.

EXAMPLES

Example 1

Reduction of 17-AAG by NQO1

In vitro studies with purified recombinant human NQO1 clearly demonstrated that reduction of 17-AAG by NQO1 in combination with NADH or NADPH generated 17-AAGH$_2$.

The metabolism of 17-AAG by NQO1 was analyzed by high performance liquid chromatography (HPLC) on a Luna C$_{18}$ reverse-phase column (5 µm, 4.6×250 mm, Phenomenex, Torrance, Calif.) at room temperature. HPLC conditions: Buffer A, 50 mM ammonium acetate, pH 4 containing 10 µM D(−) penicillamine; buffer B, acetonitrile (100%). Both buffers were continuously bubbled with N$_2$. Gradient, 20% B to 85% B over 20 min, then 85% for 4 min (flow rate of 1 ml/min). The sample injection volume was 50 µl. Liquid Chromatography-Mass Spectrometry was performed using positive ion electrospray ionization (ESI) and the mass spectra were obtained with a PE Sciex API-3000 triple quadrupole mass spectrometer (Foster City, Calif.) with a turbo ionspray source interfaced to a PE Sciex 200 HPLC system. Samples were chromatographed on a Luna C$_{18}$ reverse-phase column (5 µm, 50×2 mm (Phenomenex) using a gradient elution consisting of a 2 min initial hold at 20% B followed by an increase to 80% B over 20 min at a flow rate of 0.2 ml/min and a sample injection volume of 20 µl. Buffer A, 10 mM ammonium acetate containing 0.1% (v/v) acetic acid, pH 4.4: buffer B, 10 mM ammonium acetate in acetonitrile containing 0.1% (v/v) acetic acid. The mass spectrometer settings were: turbo ionspray temperature of 250° C., spray needle voltage at 4500 V, declustering potential (DP) at 35 V and focus plate (FP) at 125 V. Mass spectra were continuously recorded from 150 to 1000 amu every 3 s during the chromatographic analysis.

HPLC analysis of aerobic incubations of 17-AAG, NADH and rhNQO1 resulted in loss of the 17-AAG peak and generation of the more polar metabolite 17-AAGH$_2$ (FIG. 2). Formation of 17-AAGH$_2$ was NQO1-dependent and could be inhibited by addition of the NQO1 mechanism-based inhibitor 5-methoxy-1,2-dimethyl-3-[(4-nitrophenoxy)methyl]indole-4,7-dione (ES936). For these studies a single dose of 100 nM ES936 was nontoxic and resulted in >96% inhibition of NQO1 activity after 4 hr in MDA468/NQ16 cells. Inhibition of rhNQO1 by ES936 was >98%.

Identification of the more polar product as 17-AAGH$_2$ was confirmed by LC/MS (FIG. 2D). 17-AAGH$_2$ formed following reduction of 17-AAG by NQO1 and NADH co-eluted with the major product generated during sodium borohydride reduction of 17-AAG. HPLC analysis demonstrated that 90% of 17-AAG was detected in the form of the hydroquinone after reduction by NQO1 suggesting the generation of a relatively stable hydroquinone. During analysis HPLC buffers were continuously gassed with N$_2$ and a copper chelator was included. The data demonstrated that inclusion of copper (CuSO$_4$) could facilitate 17-AAGH$_2$ oxidation. The stability of 17-AAGH$_2$ in solution was measured by HPLC following reduction of 17-AAG by rhNQO1 using stoichiometric equivalents of NADH and 17-AAG (FIG. 3). In these studies the autoxidation of 17-AAGH$_2$ was followed over time in an aerobic reaction. These results demonstrated that 17-AAGH$_2$ undergoes a slow rate of autoxidation back to 17-AAG over a period of hours.

Example 2

Formation of 17-AAGH$_2$ Following Reduction by NQO1

Figure 4B:
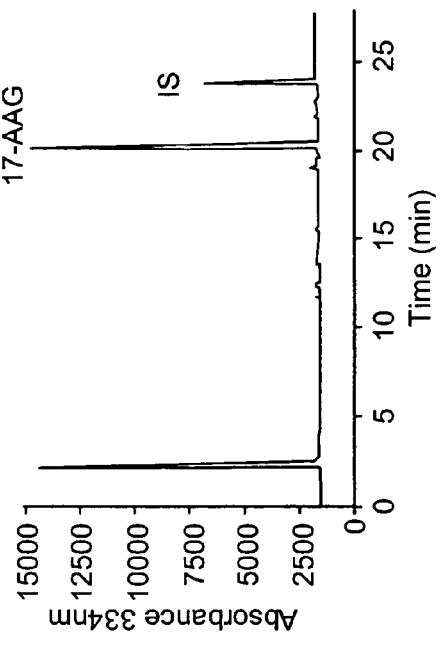
FIG. 4 shows HPLC analysis of 17-AAGH$_2$ formation by MDA468 and MDA468/NQ16 cell sonicates and intact cells. HPLC analysis confirmed the formation of 17-AAGH$_2$ following reduction of 17-AAG by MDA468/NQ16 cell sonicates (panel A) and inhibition of this reduction by ES936 (panel B). Reaction conditions: 50 μM 17-AAG, 200 μM NADH and 500 μg MDA468/NQ16 cell sonicates in 50 mM potassium phosphate buffer, pH 7.4 (1 ml) containing 1 mg/ml BSA. After 40 min reactions were stopped with an equal volume of acetonitrile containing internal standard N-phenyl-1-naphthylamine (5 μg/ml), centrifuged and the supernatant was analyzed immediately by HPLC at 334 nm. Panel A, 17-AAG, NADH and MDA468/NQ16 cell sonicates; panel B, 17-AAG, NADH, MDA468/NQ16 cell sonicates and ES936 (1 μM). Panel C, 17-AAG (open bars) and 17-AAGH$_2$ (closed bars) were measured by HPLC at 270 nm in intact MDA468 and MDA468/NQ16 cells in the presence and absence of ES936. Cells were pretreated with DMSO or ES936 (1 μM) for 20 min then treated with 17-AAG (5 μM) for 4 hrs. Following drug treatment cells were extensively washed, pelleted and lysed by the addition of acetonitrile (200 μl) containing internal standard N-phenyl-1-naphthylamine (5 μg/ml). The samples were centrifuged (13 krpm×1 min) and the supernatant was analyzed immediately. Results are expressed as mean, standard deviation, n=3.
Figure 4A:
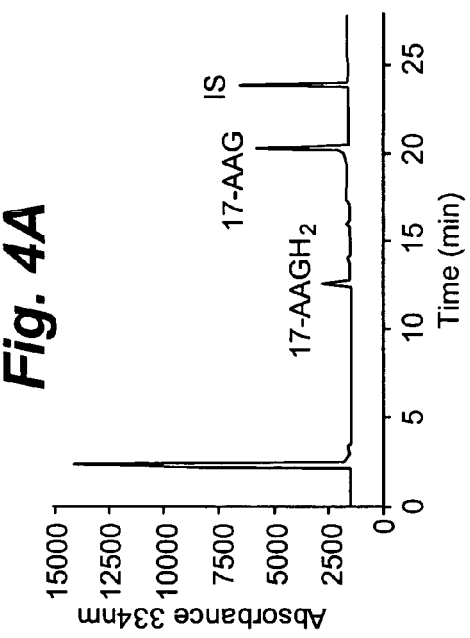

Whether 17-AAGH$_2$ could be formed in cells following reduction by NQO1 was investigated using isogenic human breast cancer cell lines. The human breast cancer cell line MDA468 and the NQO1 stably transfected cell line MDA468/NQ16 (*Clin. Cancer Res.* 2004; 10:3147-55) were grown in RPMI-1640 containing 10% (v/v) fetal bovine serum and 1% (v/v) penicillin, streptomycin and glutamine. Sonicates were prepared from MDA468 and MDA468/NQ16 cell lines by probe-sonication in ice-cold 25 mM Tris-HCl, pH 7.4 containing 250 mM sucrose and 5 µM flavin adenine dinucleotide. Protein concentrations were determined by the method of Lowry. These cell lines have been used previously to examine the role of NQO1 in anti-tumor quinone metabolism. The parental MDA468 cell lines is NQO1 null (<10 nmoles DCPIP/min/mg) due to homozygous expression of the NQO1*2 polymorphism. The stable transfection of the MDA468 cell line with human NQO1 generated the MDA468/NQ16 cell line, which has high NQO1 activity (>1,800 nmoles DCPIP/min/mg). Initial experiments were performed using cell sonicates prepared from MDA468 and MDA468/NQ16 cells. HPLC analysis of these reactions was nearly identical to results obtained with rhNQO1 (FIG. 2). Sonicates prepared from MDA468INQ16 cells readily generated 17-AAGH$_2$ (FIG. 4A). Generation of 17-AAGH$_2$ was NADH- or NADPH-dependent and could be inhibited by ES936 (FIG. 4B). No 17-AAGH$_2$ could be detected in sonicates from MDA468 cells.

To further investigate the role of NQO1 in the reduction of 17-AAG we examined whether 17-AAGH$_2$ could be generated by NQO1 in intact cells. The metabolism of 17-AAG in cells was evaluated by seeding cells at 2×10$^6$ cells per 100 mm plate (in duplicate) in complete medium for 3 days. Cells were then pretreated with 100 nM ES936 or an equal amount of DMSO for 30 min followed by 5 µM 17-AAG for additional 4 hr at 37° C. Following drug treatment, cells (1 plate) were washed extensively in phosphate buffered saline (PBS) containing 1% (v/v) BSA and then lysed on the plate by the addition of 200 µl ice-cold acetonitrile containing 1 µg/ml N-phenyl-1-naphthylamine (internal standard). Samples were centrifuged at 13 krpm for 10 sec and the supernatant was immediately analyzed by HPLC. The cell number was determined using the second plate of cells. Cells were washed in PBS then scraped in 200 µl of PBS and counted (hemocytometer).

Figure 4C:
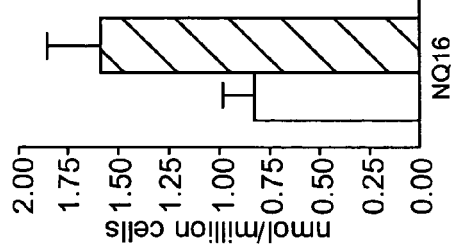

Measurement of the concentrations of 17-AAG and 17-AAGH$_2$ clearly demonstrated that 17-AAGH$_2$ could be generated in MDA468/NQ 16 cells and the formation of 17-AAGH$_2$ could be inhibited by pretreatment with ES936 (FIG. 4C). No 17-AAGH$_2$ could be detected in MDA468 cells. In addition to generating 17-AAGH$_2$, MDA468/NQ16 cells also accumulated more total drug (quinone plus hydroquinone) compared to cells treated with ES936 or parental MDA468 cells (FIG. 4C). Cell viability was >90% for both cell lines under these treatment condition (trypan blue exclusion assay).

Example 3

Growth Inhibition Induced by 17-AAG

Figure 5A:
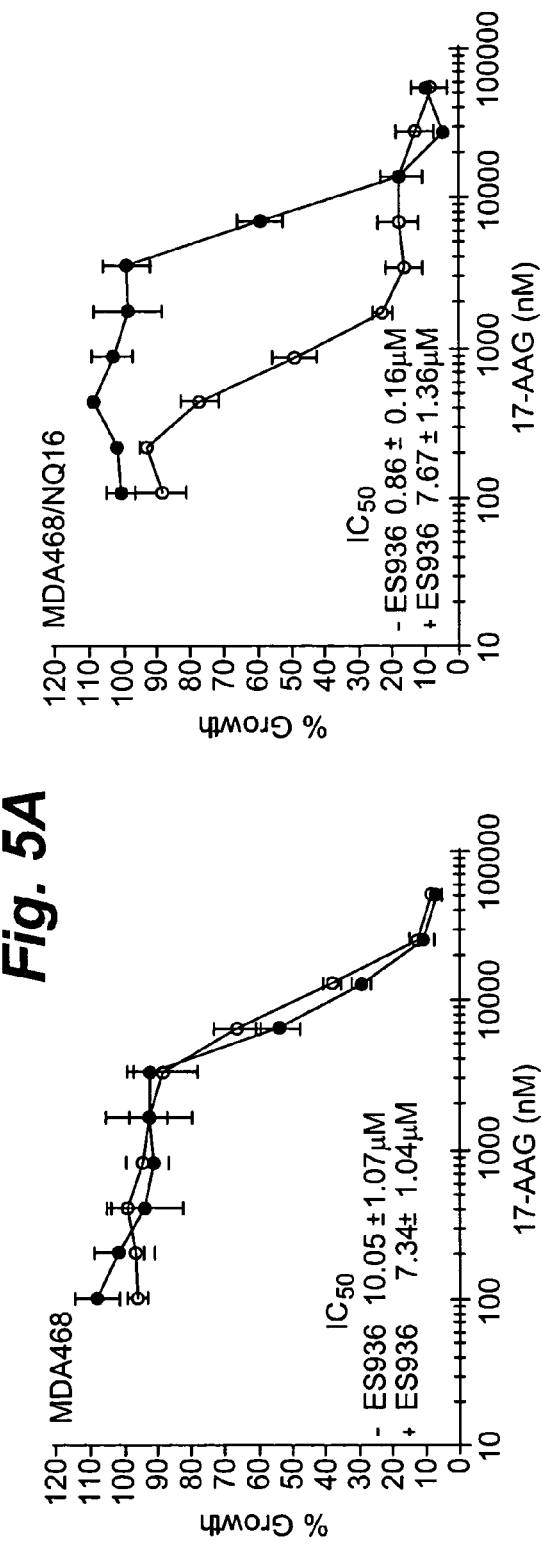
FIG. 5 shows the effect of 17-AAG on growth inhibition and Hsp90 client proteins in human breast cancer cells. Growth inhibition following 17-AAG treatment was measured by MTT analysis in MDA468 (NQO1 null) and MDA468/NQ16 (high NQO1) cell lines (panel A). Results are expressed as mean standard deviation, n=3. Panel B, effect of 17-AAG on Hsp70 and Raf-1 protein levels. Hsp70 and Raf-1 protein levels were analyzed by immunoblot analysis after treatment of MDA468 and MDA468/NQ 16 cells with 17-AAG for 8 hr. Hsp70 immunoblot analysis was performed on 25 μg whole cell sonicate. Raf-1 immunoblot analysis was performed on 50 μg whole cell sonicate. Results were confirmed in duplicate experiments. Panel C, MEK and ERK phosphorylation was analyzed by immunoblot analysis after treatment of MDA468 and MDA468/NQ 16 cells with 17-AAG. Cells were serum starved for 24 hr then treated with 17-AAG for 8 hr. pMEK/MEK immunoblot analysis was performed on 25 μg whole cell sonicate. pERK/ERK immunoblot analysis was performed on 50 μg whole cell sonicate. Results were confirmed in duplicate experiments.
Figure 5B:
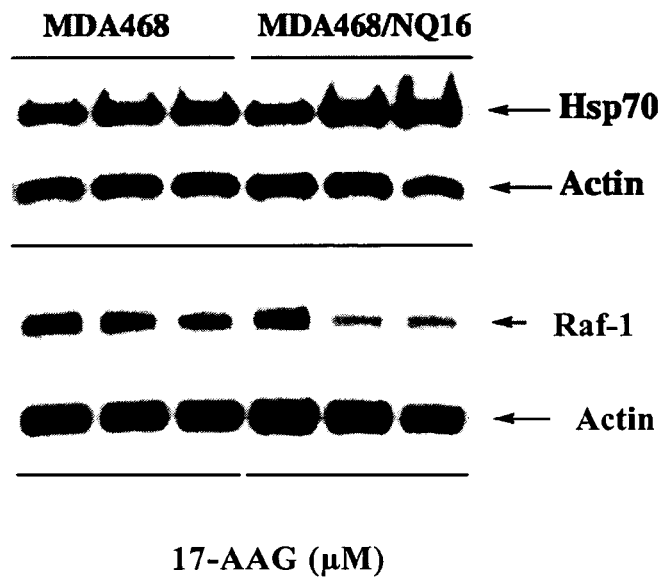
Figure 5C:
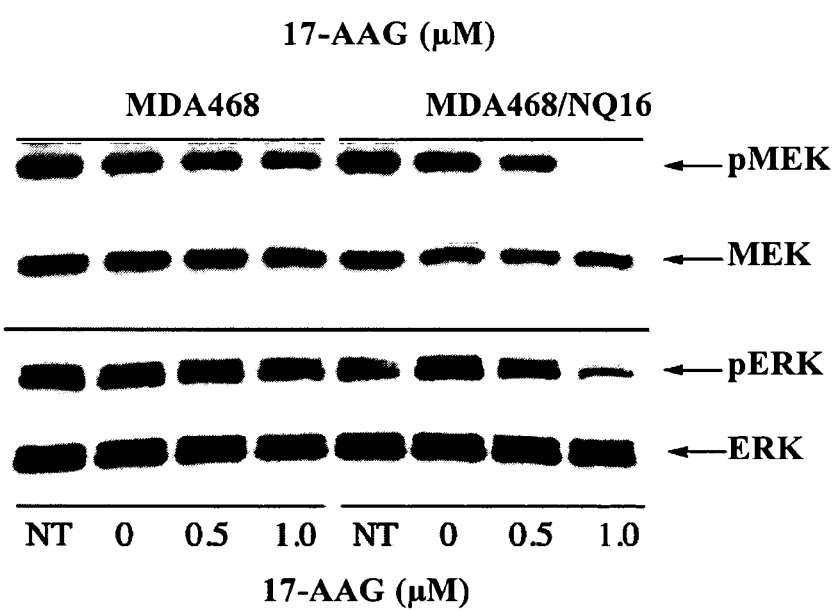

The role of NQO 1 in growth inhibition induced by 17-AAG was measured in MDA468 and MDA468/NQ16 cells using the MTT assay. Cells were seeded at 2×10$^3$ cells per well (96 well plate) in complete medium overnight. The next morning the cells were pretreated with 100 nM ES936 or an equal amount of DMSO for 30 min then exposed to 17-AAG for 4 hr, after which, cells were rinsed free of drug and incubated in fresh medium for an additional 72 hr and growth inhibition was determined using the MTT assay (FIG. 5). Results from these experiments demonstrate that MDA468/NQ16 cells have increased sensitivity to 17-AAG ($IC_{50}$ 0.86±0.16 µM) compared to parental MDA468 cells ($IC_{50}$ 10.05±1.07 µM). The sensitivity to 17-AAG can be abrogated by pretreatment with ES936 ($IC_{50}$ 7.67±1.36 µM).

The role of NQO1 in 17-AAG-induced Hsp90 inhibition in MDA468 and MDA468/NQ16 cells was also examined. To measure Hsp90 inhibition in these cells we analyzed Hsp70 induction and Raf-1 degradation as markers of Hsp90 inhibition (FIG. 5). MDA468 and MDA468/NQ16 cells were grown in 100 mm plates in complete medium to approximately 70% confluency. For Hsp70 and Raf-1 analysis cells were treated with DMSO or 17-AAG (0.5-1 µM) in 10 ml of complete medium for 8 hr. For MEK and ERK analysis cell were serum starved for 24 hr then treated with DMSO or 17-AAG (0.5-1 µM) in serum free medium for 8 hr. Following drug treatment cells were washed in PBS then lysed by the addition of RIPA buffer (50 mM Tris-HCl, pH 7.4, 0.5% (v/v) NP40) containing 1 mini-protease tablet (protease inhibitor cocktail, Roche Indianapolis Ind.) and phosphatase inhibitors (30 mM NaF, 40 mM β-glycerol phosphate, 20 mM sodium pyrophosphate, 1 mM orthovanadate, 1 mM EGTA). Lysates were probe sonicated (2s) on ice then centrifuged to remove cellular debris. Protein concentrations were determined on supernatant. Samples were heated to 70° C. in 2× Laemmli SDS sample buffer, proteins were separated by 12% SDS-PAGE (precast minigel, Bio-Rad, Hercules Calif.) and then transferred to 0.4 µm PVDF membranes. Membranes were blocked in 10 mM Tris-HCl, pH 8.0, 150 mM NaCl, 0.2% Tween-20 and 5% non-fat milk for a minimum of 1 hr at room temperature. Anti-Hsp70, anti-Raf-1, anti-MEK and anti-ERK antibodies were added for 1 hr at room temperature. Anti-phospho MEK and ERK antibodies were added overnight at 4° C. All primary antibodies were diluted 1:1,000 except actin (1:5,000). Horseradish peroxidase-labeled secondary antibodies (Jackson ImmunoResearch Labs, West Grove Pa.) were diluted 1:5000 and added for 30 min. Proteins were visualized using enhanced chemilumenscence detection.

These studies demonstrated greater Hsp70 induction and increased Raf-1 degradation in MDA468/NQ16 cells compared to MDA468 cells. Analysis of downstream (Raf-1) signaling, as reflected in MEK and ERK phosphorylation, in MDA468 and MDA468INQ16 cells treated with 17-AAG (FIG. 5) showed decreased levels of both MEK and ERK phosphorylation were observed in MDA468/NQ 16 cells compared to MDA468 cells following serum starvation. No changes in total MEK or ERK protein levels were observed (FIG. 5). These data show that a greater level of Hsp90 inhibition was occurring in NQO1 rich MDA468/NQ 16 cells compared to NQO1 deficient MDA468 cells.

Example 4

Hsp90 Inhibition by 17-AAGH$_2$

Figure 6:
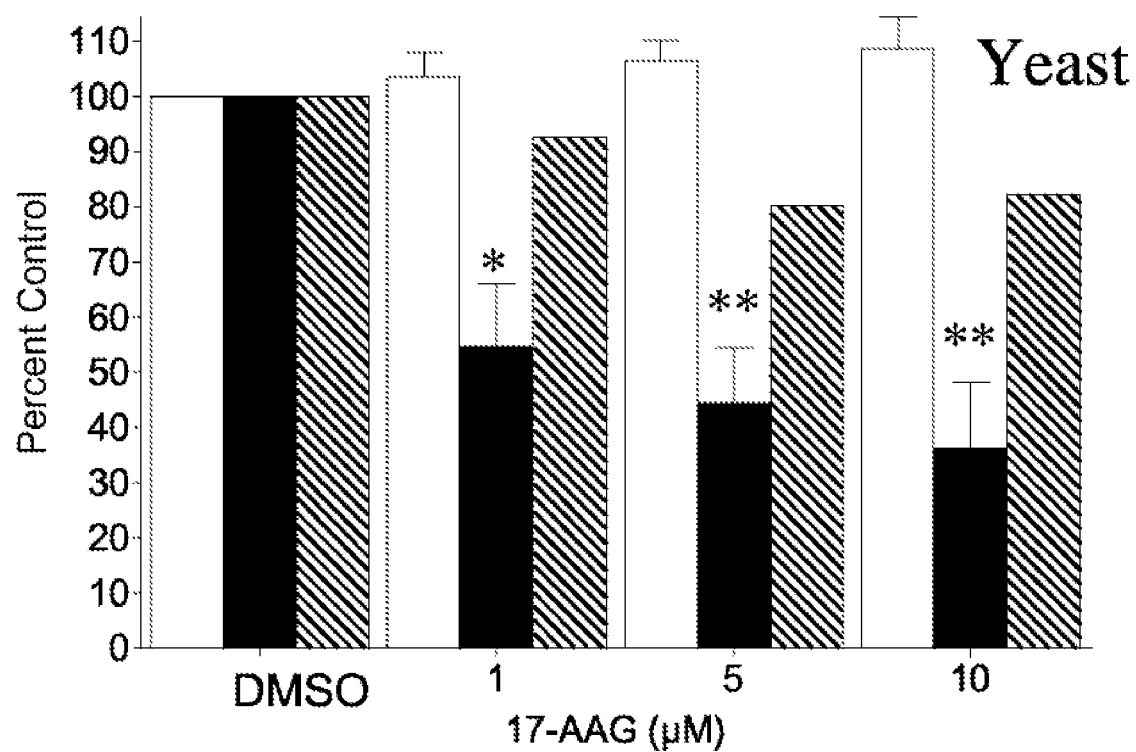
FIG. 6 shows the inhibition of yeast Hsp90 by 17-AAG and 17-AAGH$_2$. Yeast and human Hsp90 ATPase activity was measured in reactions with 17-AAG in the presence and absence of rhNQO1. Reactions with yeast Hsp90 (top panel) were analyzed after 3 hr, while reactions with human Hsp90 (bottom panel) were analyzed after 12 hr. Phosphate concentrations were measured using the malachite green assay. Open bars, 17-AAG, NADH; closed bars, 17-AAG, NADH and NQO1; hatched bars, 17-AAG, NADH, NQO1 and ES936. Where error bars are shown results are expressed as mean, standard deviation, n=3 (yeast Hsp90 results with ES936 n=2).

The relationship between 17-AAGH$_2$ formation and increased Hsp90 inhibition was confirmed by examination of the ability of 17-AAG and 17-AAGH$_2$ to inhibit the ATPase activity of purified yeast and human Hsp90 (FIG. 6). Inhibition of Hsp90 ATPase was measured by incubating 2.5 µg of purified yeast or human Hsp90 in 100 mM Tris-HCl, pH 7.4, containing 20 mM KCl, 6 mM $MgCl_2$, 400 µM NADH, 17-AAG plus or minus 3.3 µg rhNQO1 and 20 µM ES936. Reactions (25 µl) were started by the addition of 1 mM ATP and allowed to proceed at 37° C. for the indicated times. Reactions were then diluted with 225 µl of 100 mM Tris-HCl, pH 7.4, containing 20 mM KCl and 6 mM $MgCl_2$ mixed thoroughly, and 80 µl was transferred to each well (96 well plate) followed by 20 µl of malachite green reagent. After 10 min 83 mM trisodium citrate was added to stabilize the color and plates were read at 650 nm.

Results from these experiments using yeast Hsp90 demonstrated that 17-AAGH$_2$ was the active Hsp90 inhibitor. Further, a substantial decrease in ATPase activity was observed with 17-AAG in the presence of NQO1 and this could be prevented by ES936. No inhibition by 17-AAG was observed in the absence of NQO1. Results from experiments using human Hsp90 were qualitatively similar but showed some quantitative differences. In these experiments the addition of 17-AAG resulted in some inhibition of Hsp90 ATPase activity. Inhibition was significantly increased, however, by the inclusion of NQO1 and abrogated by inactivation of NQO1 by ES936 (FIG. 6).

The docking of the benzoquinone ansamycins: geldanamycin, 17-AAG, 17-AG, 17-DMAG and 17-AEP-GA and their corresponding hydroquinones into the ATP-binding site of the yeast and human Hsp90 crystal structure was studied on a Silicon Graphics Octane2 workstation. The crystallographic coordinates for the 2.5 Å structure of yeast Hsp90 (PDB: 1A4H) and the 1.9 Å structure of human Hsp90 (PDB: 1YET) were obtained from the RCSB Protein Data Bank. The Hsp90 crystal structures were visualized using the InsightII software package (Version 2000, Accelrys Inc., San Diego, USA). The Builder Module was used to add hydrogens to the protein structure and the ionizable Asp, Arg, Glu and Lys residues were corrected for physiological pH. The benzoquinone ansamycins and their corresponding hydroquinone structures were constructed, assigned the correct atom type and bond order, from the bound geldanamycin structure, in each Hsp90 crystal structure. Once constructed, the ligands were in turn superpositioned onto the bound geldanamycin structure, using the coordinated system of the protein to correctly position the ligand in the ATP-binding domain of Hsp90. The geldanamycin scaffold structure was then deleted from the protein structure and the "docked" ligand assembly was associated with the Hsp90 protein structure. For the molecular mechanics and molecular dynamics calculations the Discover Module was used, the potentials and charges of the Hsp90-ligand complex were corrected using the consistent-valence force field (CVFF). The Hsp90-ligand complex was then minimized using the conjugate-gradient method (1000 iterations). The Docking Module was used to perform the intermolecular energy calculation to determine the non-bonded interaction energy between Hsp90 and the appropriate ligand. An interface 6 Å radius subset encompassing the ligand-binding domain was selected and both the van der Waals and electrostatic (Coulombic) energies were calculated with a specified cutoff of 8 Å.

These molecular modeling studies revealed significant differences in the binding energies between the two compounds, post-minimization. The non-bonded interaction energy or binding energy is the sum of the van der Waals and electrostatic energies, the measure of the affinity between Hsp90 and the particular ligand. In both the yeast and human Hsp90 crystal structures, the hydroquinone had greater non-bonded interaction energy, or affinity for the ATP-binding domain, than the parent quinone. These data show that the hydroquinone form of the benzoquinone ansamycins are more potent inhibitors of Hsp90. Following minimization, the Hsp90-ligand complex was visualized in order to identify important amino acid residues in the ATP-binding domain that interact via hydrogen bonding with the ligand investigated, there was no significant change in the global conformation of Hsp90. However, additional hydrogen bonding interactions between the hydroquinone moiety and Hsp90 that resulted in a greater binding energy (Tables 1-10).

TABLE 1

The interaction energy ($E_{total}$), van der Waals ($E_{vdw}$), electrostatic energy ($E_{elect}$) and hydrogen-bonding interactions for geldanamycin (GDM) and the corresponding hydroquinone (GDMH$_2$) with the yeast Hsp90 crystal structure.

| COMPOUND | $E_{vdw}$ (kcal/mol) | $E_{elect}$ (kcal/mol) | $E_{total}$ (kcal/mol) | H-BOND INTERACTION AMINO ACID/ SOLVENT | LIGAND | H-BOND DISTANCE (Å) |
|---|---|---|---|---|---|---|
| GDM | −37.9 | −13.0 | −50.9 | ASP-79 | CARBAMATE NH$_2$ | 1.99 |
| | | | | LYS+98 | QUINONE C=O | 2.02 |
| | | | | PHE124 | AMIDE C=O | 2.09 |
| | | | | HOH400 | CARBAMATE C=O | 2.06 |
| | | | | HOH402 | CARBAMATE NH$_2$ | 2.27 |
| | | | | HOH403 | METHOXY (ANSA) OCH$_3$ | 2.29 |
| | | | | HOH405 | HYDROXY (ANSA) OH | 2.08 |
| | | | | HOH407 | QUINONE C=O | 1.93 |
| | | | | HOH528 | AMIDE NH | 2.18 |
| GDMH$_2$ | −37.0 | −33.8 | −70.7 | ASP-40 | HYDROQUINONE O—H | 2.15 |
| | | | | ASP-79 | CARBAMATE NH$_2$ | 2.06 |
| | | | | LYS+98 | HYDROQUINONE C—O | 2.16 |
| | | | | PHE124 | AMIDE C=O | 2.49 |
| | | | | HOH400 | CARBAMATE C=O | 2.25 |
| | | | | HOH402 | CARBAMATE NH$_2$ | 2.24 |
| | | | | HOH403 | METHOXY (ANSA) OCH$_3$ | 2.31 |
| | | | | HOH403 | CARBAMATE R—O—CONH$_2$ | 2.50 |
| | | | | HOH405 | HYDROXY (ANSA) OH | 2.04 |
| | | | | HOH407 | HYDROQUINONE O—H | 2.04 |
| | | | | HOH529 | AMIDE NH | 2.05 |

TABLE 2

The interaction energy ($E_{total}$), van der Waals ($E_{vdw}$), electrostatic energy ($E_{elect}$) and hydrogen-bonding interactions for 17-amino-17-demethoxy-geldanamycin (17-AG) and the corresponding hydroquinone (17-AGH$_2$) with the yeast Hsp90 crystal structure.

| COMPOUND | $E_{vdw}$ (kcal/mol) | $E_{elect}$ (kcal/mol) | $E_{total}$ (kcal/mol) | AMINO ACID/ SOLVENT | LIGAND | H-BOND DISTANCE (Å) |
|---|---|---|---|---|---|---|
| 17-AG | −29.5 | −21.7 | −51.2 | ASP-40 | AMINE —NH$_2$ | 2.10 |
| | | | | ASP-79 | CARBAMATE NH$_2$ | 1.96 |
| | | | | LYS+98 | QUINONE C=O | 1.93 |
| | | | | PHE124 | AMIDE C=O | 2.42 |
| | | | | HOH400 | CARBAMATE C=O | 2.06 |
| | | | | HOH403 | CARBAMATE NH$_2$ | 2.18 |
| | | | | HOH405 | HYDROXY (ANSA) OH | 2.03 |
| | | | | HOH405 | METHOXY (ANSA) OCH$_3$ | 2.02 |
| | | | | HOH407 | QUINONE C=O | 1.76 |
| 17-AGH$_2$ | −35.0 | −38.1 | −73.0 | ASP-40 | HYDROQUINONE O—H | 1.87 |
| | | | | ASP-40 | AMINE —NH$_2$ | 2.11 |
| | | | | ASP-79 | CARBAMATE NH$_2$ | 2.02 |
| | | | | LYS+98 | HYDROQUINONE C—O | 2.44 |
| | | | | PHE124 | AMIDE C=O | 2.34 |
| | | | | HOH400 | CARBAMATE C=O | 2.00 |
| | | | | HOH402 | CARBAMATE NH$_2$ | 2.27 |
| | | | | HOH403 | METHOXY (ANSA) OCH$_3$ | 2.38 |
| | | | | HOH405 | HYDROXY (ANSA) OH | 2.38 |

TABLE 3

The interaction energy ($E_{total}$), van der Waals ($E_{vdw}$), electrostatic energy ($E_{elect}$) and hydrogen-bonding interactions for 17-demethoxy-17-[[2-(dimethylamino)ethyl]amino]-geldanamycin (17-AAG) and the corresponding hydroquinone (17AAGH$_2$) with the yeast Hsp90 crystal structure.

| COMPOUND | $E_{vdw}$ (kcal/mol) | $E_{elect}$ (kcal/mol) | $E_{total}$ (kcal/mol) | AMINO ACID/ SOLVENT | LIGAND | H-BOND DISTANCE (Å) |
|---|---|---|---|---|---|---|
| 17-AAG | −36.6 | −25.0 | −61.6 | ASP-79 | CARBAMATE NH$_2$ | 2.03 |
| | | | | LYS+98 | QUINONE C=O | 1.91 |
| | | | | HOH400 | CARBAMATE C=O | 2.04 |
| | | | | HOH403 | METHOXY (ANSA) OCH$_3$ | 2.47 |
| | | | | HOH403 | CARBAMATE R—O—CONH$_2$ | 2.32 |
| | | | | HOH405 | HYDROXY (ANSA) OH | 2.39 |
| | | | | HOH407 | QUINONE C=O | 1.83 |
| | | | | HOH529 | AMIDE NH | 1.89 |
| 17-AAGH$_2$ | −39.1 | −29.2 | −68.2 | ASP-40 | HYDROQUINONE O—H | 2.40 |
| | | | | ASP-79 | CARBAMATE NH$_2$ | 2.00 |
| | | | | PHE124 | AMIDE C=O | 2.35 |
| | | | | HOH400 | CARBAMATE C=O | 2.05 |
| | | | | HOH402 | CARBAMATE NH$_2$ | 2.25 |
| | | | | HOH403 | METHOXY (ANSA) OCH$_3$ | 2.30 |
| | | | | HOH403 | CARBAMATE R—O—CONH$_2$ | 2.46 |
| | | | | HOH405 | HYDROXY (ANSA) OH | 2.38 |
| | | | | HOH407 | HYDROQUINONE O—H | 2.33 |

TABLE 4

The interaction energy ($E_{total}$), van der Waals ($E_{vdw}$), electrostatic energy ($E_{elect}$) and hydrogen-bonding interactions for 17-demethoxy-17-[[2-(dimethylamino)ethyl]amino]-geldanamycin (17-DMAG) and the corresponding hydroquinone (17-DMAGH$_2$) with the yeast Hsp90 crystal structure.

| COMPOUND | $E_{vdw}$ (kcal/mol) | $E_{elect}$ (kcal/mol) | $E_{total}$ (kcal/mol) | AMINO ACID/ SOLVENT | LIGAND | H-BOND DISTANCE (Å) |
|---|---|---|---|---|---|---|
| 17-DMAG | −26.5 | −27.7 | −54.2 | ASP-79 | CARBAMATE NH$_2$ | 2.04 |
| | | | | LYS+98 | QUINONE C=O | 1.74 |
| | | | | HOH400 | CARBAMATE C=O | 2.14 |
| | | | | HOH402 | CARBAMATE NH$_2$ | 2.22 |

TABLE 4-continued

The interaction energy ($E_{total}$), van der Waals ($E_{vdw}$), electrostatic energy ($E_{elect}$) and hydrogen-bonding interactions for 17-demethoxy-17-[[2-(dimethylamino)ethyl]amino]-geldanamycin (17-DMAG) and the corresponding hydroquinone (17-DMAGH$_2$) with the yeast Hsp90 crystal structure.

| COMPOUND | $E_{vdw}$ (kcal/mol) | $E_{elect}$ (kcal/mol) | $E_{total}$ (kcal/mol) | H-BOND INTERACTION | | H-BOND DISTANCE (Å) |
|---|---|---|---|---|---|---|
| | | | | AMINO ACID/ SOLVENT | LIGAND | |
| | | | | HOH403 | METHOXY (ANSA) OCH$_3$ | 2.35 |
| | | | | HOH403 | CARBAMATE R—O—CONH$_2$ | 2.18 |
| | | | | HOH405 | HYDROXY (ANSA) OH | 2.32 |
| | | | | HOH407 | QUINONE C=O | 1.65 |
| | | | | HOH485 | AMINE R—N(CH$_3$)$_2$ | 1.95 |
| | | | | HOH529 | AMIDE NH | 1.95 |
| 17-DMAGH$_2$ | −30.9 | −28.1 | −58.9 | ASP-40 | HYDROQUINONE O—H | 2.00 |
| | | | | ASP-79 | CARBAMATE NH$_2$ | 1.86 |
| | | | | PHE124 | AMIDE C=O | 2.14 |
| | | | | HOH400 | CARBAMATE C=O | 1.99 |
| | | | | HOH402 | CARBAMATE NH$_2$ | 2.35 |
| | | | | HOH403 | METHOXY (ANSA) OCH$_3$ | 2.38 |
| | | | | HOH405 | HYDROXY (ANSA) OH | 1.93 |
| | | | | HOH529 | AMIDE NH | 2.07 |

TABLE 5

The interaction energy ($E_{total}$), van der Waals ($E_{vdw}$), electrostatic energy ($E_{elect}$) and hydrogen-bonding interactions for 17-demethoxy-17-[[2-(pyrrolidin-1-yl)ethyl]amino-geldanamycin (17-AEP-GA) and the corresponding hydroquinone (17-AEP-GAH$_2$) with the yeast Hsp90 crystal structure.

| COMPOUND | $E_{vdw}$ (kcal/mol) | $E_{elect}$ (kcal/mol) | $E_{total}$ (kcal/mol) | H-BOND INTERACTION | | H-BOND DISTANCE (Å) |
|---|---|---|---|---|---|---|
| | | | | AMINO ACID/ SOLVENT | LIGAND | |
| 17-AEP-GA | −27.9 | −24.8 | −52.7 | ASP-79 | CARBAMATE NH$_2$ | 2.12 |
| | | | | LYS+98 | QUINONE C=O | 1.66 |
| | | | | HOH400 | CARBAMATE C=O | 2.39 |
| | | | | HOH402 | CARBAMATE NH$_2$ | 2.40 |
| | | | | HOH403 | METHOXY (ANSA) OCH$_3$ | 2.49 |
| | | | | HOH403 | CARBAMATE R—O—CONH$_2$ | 2.20 |
| | | | | HOH405 | HYDROXY (ANSA) OH | 2.08 |
| | | | | HOH407 | QUINONE C=O | 1.69 |
| | | | | HOH529 | AMIDE NH | 2.13 |
| 17-AEP-GAH$_2$ | −28.3 | −27.6 | −55.9 | ASP-40 | HYDROQUINONE O—H | 2.24 |
| | | | | ASP-79 | CARBAMATE NH$_2$ | 2.07 |
| | | | | LYS+98 | HYDROQUINONE O—H | 2.49 |
| | | | | PHE124 | AMIDE C=O | 1.91 |
| | | | | HOH400 | CARBAMATE C=O | 2.25 |
| | | | | HOH402 | CARBAMATE NH$_2$ | 2.25 |
| | | | | HOH403 | METHOXY (ANSA) OCH$_3$ | 2.33 |
| | | | | HOH403 | CARBAMATE R—O—CONH$_2$ | 2.43 |
| | | | | HOH405 | HYDROXY (ANSA) OH | 2.14 |
| | | | | HOH407 | HYDROQUINONE | 1.94 |

TABLE 6

The interaction energy ($E_{total}$), van der Waals ($E_{vdw}$), electrostatic energy ($E_{elect}$) and hydrogen-bonding interactions for geldanamycin (GDM) and the corresponding hydroquinone (GDMH$_2$) with the human Hsp90 crystal structure.

| COMPOUND | $E_{vdw}$ (kcal/mol) | $E_{elect}$ (kcal/mol) | $E_{total}$ (kcal/mol) | H-BOND INTERACTION | | H-BOND DISTANCE (Å) |
|---|---|---|---|---|---|---|
| | | | | AMINO ACID/ SOLVENT | LIGAND | |
| GDM | −23.3 | −2.9 | −26.2 | LYS+58 | HYDROXY (ANSA) O—H | 1.66 |
| | | | | ASP-93 | CARBAMATE NH$_2$ | 2.05 |
| | | | | LYS+112 | QUINONE C=O | 1.83 |
| | | | | PHE138 | AMIDE C=O | 2.06 |
| | | | | HOH132 | QUINONE C=O | 2.01 |
| | | | | HOH245 | CARBAMATE C=O | 2.10 |

TABLE 6-continued

The interaction energy ($E_{total}$), van der Waals ($E_{vdw}$), electrostatic energy ($E_{elect}$) and hydrogen-bonding interactions for geldanamycin (GDM) and the corresponding hydroquinone ($GDMH_2$) with the human Hsp90 crystal structure.

| COMPOUND | $E_{vdw}$ (kcal/mol) | $E_{elect}$ (kcal/mol) | $E_{total}$ (kcal/mol) | H-BOND INTERACTION AMINO ACID/ SOLVENT | LIGAND | H-BOND DISTANCE (Å) |
|---|---|---|---|---|---|---|
| $GDMH_2$ | −22.4 | −12.1 | −34.9 | ASP-54 | HYDROQUINONE O—H | 1.98 |
| | | | | LYS+58 | HYDROXY (ANSA) O—H | 1.76 |
| | | | | LYS+58 | METHOXY (ANSA) $OCH_3$ | 2.38 |
| | | | | ASP-93 | CARBAMATE $NH_2$ | 1.98 |
| | | | | LYS+112 | HYDROQUINONE O—H | 1.96 |
| | | | | PHE138 | AMIDE C=O | 2.03 |
| | | | | HOH106 | CARBAMATE $NH_2$ | 2.23 |
| | | | | HOH245 | CARBAMATE C=O | 2.04 |
| | | | | HOH246 | CARBAMATE R—O—$CONH_2$ | 2.42 |
| | | | | HOH246 | METHOXY (ANSA) $OCH_3$ | 2.25 |

TABLE 7

The interaction energy ($E_{total}$), van der Waals ($E_{vdw}$), electrostatic energy ($E_{elect}$) and hydrogen-bonding interactions for 17-amino-17-demethoxy-geldanamycin (17-AG) and the corresponding hydroquinone (17-$AGH_2$) with the human Hsp90 crystal structure.

| COMPOUND | $E_{vdw}$ (kcal/mol) | $E_{elect}$ (kcal/mol) | $E_{total}$ (kcal/mol) | H-BOND INTERACTION AMINO ACID/ SOLVENT | LIGAND | H-BOND DISTANCE (Å) |
|---|---|---|---|---|---|---|
| 17-AG | −27.8 | −6.2 | −33.9 | ASP-54 | AMINO $NH_2$ | 2.44 |
| | | | | LYS+58 | HYDROXY (ANSA) O—H | 1.69 |
| | | | | ASP-93 | CARBAMATE $NH_2$ | 2.03 |
| | | | | LYS+112 | QUINONE C=O | 1.76 |
| | | | | PHE138 | AMIDE C=O | 2.13 |
| | | | | HOH132 | QUINONE C=O | 2.10 |
| | | | | HOH245 | CARBAMATE C=O | 2.11 |
| 17-$AGH_2$ | −28.3 | −15.2 | −43.6 | ASP-54 | HYDROQUINONE O—H | 1.89 |
| | | | | ASP-54 | AMINE $NH_2$ | 2.19 |
| | | | | LYS+58 | HYDROXY (ANSA) O—H | 2.42 |
| | | | | LYS+58 | AMINE NHR | 1.82 |
| | | | | ASP-93 | CARBAMATE $NH_2$ | 1.99 |
| | | | | LYS+112 | HYDROQUINONE O—H | 1.93 |
| | | | | PHE138 | AMIDE C=O | 2.00 |
| | | | | HOH106 | CARBAMATE $NH_2$ | 2.27 |
| | | | | HOH245 | CARBAMATE C=O | 2.09 |
| | | | | HOH246 | CARBAMATE R—O—$CONH_2$ | 2.47 |
| | | | | HOH246 | METHOXY (ANSA) $OCH_3$ | 2.32 |

TABLE 8

The interaction energy ($E_{total}$), van der Waals ($E_{vdw}$), electrostatic energy ($E_{elect}$) and hydrogen-bonding interactions for 17-demethoxy-17-[[2-(dimethylamino)ethyl]amino]-geldanamycin (17-AAG) and the corresponding hydroquinone (17$AAGH_2$) with the human Hsp90 crystal structure.

| COMPOUND | $E_{vdw}$ (kcal/mol) | $E_{elect}$ (kcal/mol) | $E_{total}$ (kcal/mol) | H-BOND INTERACTION AMINO ACID/ SOLVENT | LIGAND | H-BOND DISTANCE (Å) |
|---|---|---|---|---|---|---|
| 17-AAG | −23.5 | −4.6 | −28.1 | LYS+58 | HYDROXY (ANSA) O—H | 1.69 |
| | | | | ASP-93 | CARBAMATE $NH_2$ | 2.06 |
| | | | | LYS+112 | QUINONE C=O | 1.84 |
| | | | | PHE138 | AMIDE C=O | 2.08 |
| | | | | HOH106 | CARBAMATE $NH_2$ | 2.32 |
| | | | | HOH132 | QUINONE C=O | 2.10 |
| | | | | HOH245 | CARBAMATE C=O | 2.11 |
| | | | | HOH246 | METHOXY (ANSA) $OCH_3$ | 2.37 |
| 17-$AAGH_2$ | −22.3 | −15.5 | −37.5 | ASP-54 | HYDROQUINONE O—H | 1.96 |
| | | | | ASP-54 | AMINE NHR | 2.27 |
| | | | | LYS+58 | HYDROXY (ANSA) O—H | 1.72 |
| | | | | LYS+58 | AMINE NHR | 2.44 |

TABLE 8-continued

The interaction energy ($E_{total}$), van der Waals ($E_{vdw}$), electrostatic energy ($E_{elect}$) and hydrogen-bonding interactions for 17-demethoxy-17-[[2-(dimethylamino)ethyl]amino]-geldanamycin (17-AAG) and the corresponding hydroquinone (17AAGH$_2$) with the human Hsp90 crystal structure.

| COMPOUND | $E_{vdw}$ (kcal/mol) | $E_{elect}$ (kcal/mol) | $E_{total}$ (kcal/mol) | AMINO ACID/ SOLVENT | LIGAND | H-BOND DISTANCE (Å) |
|---|---|---|---|---|---|---|
| | | | | ASP-93 | CARBAMATE NH$_2$ | 2.04 |
| | | | | LYS+112 | HYDROQUINONE O—H | 1.90 |
| | | | | PHE138 | AMIDE C=O | 2.00 |
| | | | | HOH106 | CARBAMATE NH$_2$ | 2.27 |
| | | | | HOH245 | CARBAMATE C=O | 2.05 |
| | | | | HOH246 | CARBAMATE R—O—CONH$_2$ | 2.47 |
| | | | | HOH246 | METHOXY (ANSA) OCH$_3$ | 2.32 |

TABLE 9

The interaction energy ($E_{total}$), van der Waals ($E_{vdw}$), electrostatic energy ($E_{elect}$) and hydrogen-bonding interactions for 17-demethoxy-17-[[2-(dimethylamino)ethyl]amino]-geldanamycin (17-DMAG) and the corresponding hydroquinone (17-DMAGH$_2$) with the human Hsp90 crystal structure.

| COMPOUND | $E_{vdw}$ (kcal/mol) | $E_{elect}$ (kcal/mol) | $E_{total}$ (kcal/mol) | AMINO ACID/ SOLVENT | LIGAND | H-BOND DISTANCE (Å) |
|---|---|---|---|---|---|---|
| 17-DMAG | −25.2 | −20.1 | −45.3 | LYS+58 | HYDROXY (ANSA) O—H | 1.68 |
| | | | | ASP-93 | CARBAMATE NH$_2$ | 2.03 |
| | | | | LYS+112 | QUINONE C=O | 1.82 |
| | | | | PHE138 | AMIDE C=O | 2.16 |
| | | | | HOH132 | QUINONE C=O | 1.98 |
| | | | | HOH245 | CARBAMATE C=O | 2.13 |
| 17-DMAGH$_2$ | −25.1 | −26.3 | −51.4 | ASP-54 | HYDROQUINONE O—H | 1.98 |
| | | | | ASP-54 | AMINE NHR | 2.27 |
| | | | | LYS+58 | HYDROXY (ANSA) O—H | 1.74 |
| | | | | LYS+58 | AMINE NHR | 2.45 |
| | | | | ASP-93 | CARBAMATE NH$_2$ | 2.07 |
| | | | | LYS+112 | HYDROQUINONE O—H | 1.91 |
| | | | | PHE138 | AMIDE C=O | 2.04 |
| | | | | HOH106 | CARBAMATE NH$_2$ | 2.30 |
| | | | | HOH245 | CARBAMATE C=O | 2.11 |
| | | | | HOH246 | METHOXY (ANSA) OCH$_3$ | 2.29 |

TABLE 10

The interaction energy ($E_{total}$), van der Waals ($E_{vdw}$), electrostatic energy ($E_{elect}$) and hydrogen-bonding interactions for 17-demethoxy-17-[[2-(pyrrolidin-1-yl)ethyl]amino-geldanamycin (17-AEP-GA) and the corresponding hydroquinone (17-AEP-GAH$_2$) with the human Hsp90 crystal structure.

| COMPOUND | $E_{vdw}$ (kcal/mol) | $E_{elect}$ (kcal/mol) | $E_{total}$ (kcal/mol) | AMINO ACID/ SOLVENT | LIGAND | H-BOND DISTANCE (Å) |
|---|---|---|---|---|---|---|
| 17-AEP-GA | −24.5 | −14.4 | −38.9 | LYS+58 | HYDROXY (ANSA) O—H | 1.68 |
| | | | | ASP-93 | CARBAMATE NH$_2$ | 2.05 |
| | | | | LYS+112 | QUINONE C=O | 1.79 |
| | | | | PHE138 | AMIDE C=O | 2.09 |
| | | | | HOH106 | CARBAMATE NH$_2$ | 2.35 |
| | | | | HOH132 | QUINONE C=O | 2.09 |
| | | | | HOH245 | CARBAMATE C=O | 2.12 |
| | | | | HOH245 | METHOXY (ANSA) OCH$_3$ | 2.44 |
| 17-AEP-GAH$_2$ | −22.1 | −25.1 | −47.2 | ASP-54 | HYDROQUINONE O—H | 2.00 |
| | | | | ASP-54 | AMINE NHR | 2.32 |
| | | | | LYS+58 | HYDROXY (ANSA) O—H | 1.72 |
| | | | | LYS+58 | AMINE NHR | 2.36 |
| | | | | ASP-93 | CARBAMATE NH$_2$ | 2.07 |
| | | | | LYS+112 | HYDROQUINONE O—H | 1.92 |
| | | | | PHE138 | AMIDE C=O | 2.04 |

TABLE 10-continued

The interaction energy ($E_{total}$), van der Waals ($E_{vdw}$), electrostatic energy ($E_{elect}$) and hydrogen-bonding interactions for 17-demethoxy-17-[[2-(pyrrolidin-1-yl)ethyl]amino-geldanamycin (17-AEP-GA) and the corresponding hydroquinone (17-AEP-GAH$_2$) with the human Hsp90 crystal structure.

| COMPOUND | $E_{vdw}$ (kcal/mol) | $E_{elect}$ (kcal/mol) | $E_{total}$ (kcal/mol) | H-BOND INTERACTION | | H-BOND DISTANCE (Å) |
|---|---|---|---|---|---|---|
| | | | | AMINO ACID/ SOLVENT | LIGAND | |
| | | | | HOH106 | CARBAMATE NH$_2$ | 2.30 |
| | | | | HOH213 | HYDROQUINONE O—H | 2.49 |
| | | | | HOH245 | CARBAMATE C=O | 2.07 |
| | | | | HOH246 | CARBAMATE R—O—CONH$_2$ | 2.46 |
| | | | | HOH246 | METHOXY (ANSA) OCH$_3$ | 2.35 |

In the ATP-binding domain of yeast Hsp90, the C21 ketone of the benzoquinone ansamycins hydrogen bonds with the amine of Lys98 and the C18 ketone, of the quinone ring system, interacts with a water molecule that in turn contacts Asp40. Whereas, in the corresponding hydroquinone of 17-AAG and 17-DMAG, the oxygen atom of the C21 hydroxyl does not interact directly via hydrogen bonding with Lys98. The hydrogen atom of the C18 hydroxyl, in the hydroquinone forms, allows interaction with an oxygen atom of the carboxylate side chain of Asp40. No interactions were observed with yeast Hsp90 protein and the 17-substituent indicating that the R$_3$ side chain is orientated into solvent and does not directly interfere with the binding of the ligand (quinone or hydroquinone) to the target site.

Similar interactions were observed in the ATP-binding domain of human Hsp90 with the benzoquinone ansamycins, the C21 ketone hydrogen bonds with the amine of Lys112 and the C18 ketone interacts with a water molecule that makes contact with Asn51. In both the benzoquinone ansamycins and their corresponding hydroquinones, the amide of the ansa ring interacts with the backbone nitrogen of Phe138 and the C11 hydroxyl group, of the ansa ring, hydrogen bonds with the amine of Lys58 in human Hsp90. However, there is a rearrangement of protein-ligand interactions in the binding site accompanying the substitution of the hydroquinone for the benzoquinone moiety. The interaction of the C21 hydroxyl and the amine of the Lys112 is maintained in all the hydroquinone forms, although at a greater hydrogen bond distance, in contrast to that observed with yeast Hsp90. The C18 hydroxyl interacts with Asp54, as a result, the hydroquinone moiety enables the ansamycin ring to adopt a more compact C-shaped clamp conformation around the amino acid residues of helix-2. This allows hydrogen bonding between favourable 17-substituents and the carboxylate side chain of Asp54 and/or the side chain amine of Lys58. The hydrogen bonding between the 17-substituent and Asp54 and/or Lys58 are the only protein-ligand interactions provided by the R$_3$ group, the large side chains are orientated away from the binding site and into the solvent, this restricts comparison across the benzoquinone ansamycin series.

The foregoing description of the present invention has been presented for purposes of illustration and description. Furthermore, the description is not intended to limit the invention to the form disclosed herein. Consequently, variations and modifications commensurate with the above teachings, and the skill or knowledge of the relevant art, are within the scope of the present invention. The embodiment described hereinabove is further intended to explain the best mode known for practicing the invention and to enable others skilled in the art to utilize the invention in such, or other, embodiments and with various modifications required by the particular applications or uses of the present invention. It is intended that the appended claims be construed to include alternative embodiments to the extent permitted by the prior art.

What is claimed is:

1. A purified compound having the chemical structure:

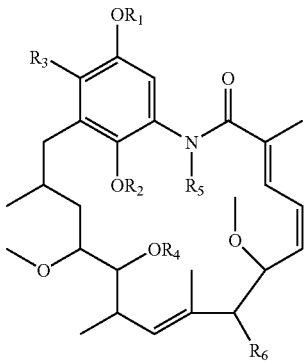

or a pharmaceutically-acceptable salt thereof;
wherein:

R$_1$ and R$_2$ are independently C$_{2-6}$ alkyl, C$_{3-8}$ cycloalkyl, C(=O)C$_{1-10}$ alkyl, C(=O)(CH$_2$)$_n$-cycloalkyl, C(=O)(CH$_2$)$_n$-aryl, wherein n=1-10, alkoxy, alkylthiol, glycoside, glucuronide or sulfate, C(=O)CH(X)NH$_2$, and C(=O)CH(X)OH wherein X=an amino acid side chain;

R$_3$ is H, NHCH$_2$CH=CH$_2$, NHCH$_2$CH$_2$N(CH$_3$)$_2$, NHCH$_2$CH$_2$NC$_4$H$_8$, azetidinyl, furfuryl, morpholinyl, piperidinyl, piperazinyl, pyrrolidinyl, tetrahydrofurfuryl, 2-methyl-1-aziridinyl, (dimethylamino)methyl-1-aziridinyl, 3-(dimethylamino)-1-azetidinyl, 3-hydroxy-1-pyrrolidinyl, 3,4-dihydroxy-1-pyrrolidinyl, or NR$_7$R$_8$, OR$_7$, SR$_7$, wherein R$_7$ and R$_8$ are independently alkenyl, alkynyl, alkoxy, alkylhalide, alkyldihalide, amine, cycloalkyl, carboxyalkyl, (acetylamino)alkyl, (dimethylamino)alkyl, 1-(methoxymethyl)alkyl, 2-(1,3-dioxolan-2-yl)alkyl, 4,4-dimethoxybutyl, [[(1,1-dimethylethoxy)carbonyl]amino]alkyl, [[(1,1-dimethylethoxy)carbonyl]alkylamino]alkyl, 1-(hydroxymethyl)alkyl, 1-(hydroxymethyl)-2-methylalkyl, 2-(hydroxymethyl)cycloalkyl, (diethylamino)alkyl, 2-(dimethylamino)-1-methylethyl, (ethylmethylamino)alkyl, [(2-fluoroethyl)methylamino]alkyl, [(2,2-difluoroethyl)methylamino]alkyl, [bis(2-hydroxyethyl)

amino]alkyl, (dimethyloxidoamino)alkyl, (trimethylammonio)alkyl, (1-aziridinyl)alkyl, (1-aziridinylmethyl)alkyl, (1-azetidinyl)alkyl, (2-deoxy-D-glucos-2-yl), (6-deoxy-D-glucos-6-yl), (1H-imidazol-4-yl) alkyl, (1-methyl-1H-imidazol-4-yl)alkyl, (1-methyl-1H-imidazol-5-yl)alkyl, (4-morpholinyl)alkyl, (4-pyridinyl)alkyl, (1-piperidinyl)alkyl, (1-piperazinyl) alkyl, (1-pyrrolidinyl)alkyl, (1-ethyl-2-pyrrolidinyl)methyl, or 2-(N-methyl-pyrrolidin-2-yl)ethyl; and wherein when $R_1$ and $R_2$ are both H, $R_3$ is not $NH_2$;

$R_4$ and $R_5$ are independently H, $C_{1-6}$ alkyl, $C_{3-8}$ cycloalkyl, $C(=O)C_{1-10}$ alkyl, $C(=O)(CH_2)_n$-aryl, $C(=O)(CH_2)_n$-cycloalkyl, alkoxy, alkylthiol or sulfate, wherein n=1-10; and, $R_6$ is O, $OC(=O)NH_2$, $OC(=O)C_{1-10}$ alkyl, $OSO_2OH$, $OC(=O)OSO_2OH$ and $OC(=O)NR_9R_{10}$ wherein $R_9$ and $R_{10}$ are independently H and $C_{1-10}$ alkyl.

2. A purified compound having the chemical structure:

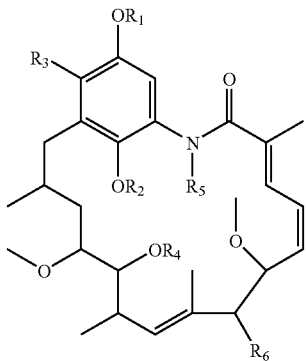

or a pharmaceutically-acceptable salt thereof; wherein:

$R_1$ and $R_2$ are independently H, $C_{1-6}$ alkyl, $C_{3-8}$ cycloalkyl, $C(=O)C_{1-10}$ alkyl, $C(=O)(CH_2)_n$-cycloalkyl, $C(=O)(CH_2)_n$-aryl, wherein n=1-10, alkoxy, alkylthiol, glycoside, glucuronide or sulfate, $C(=O)CH(X)NH_2$, and $C(=O)CH(X)OH$, wherein X=an amino acid side chain;

$R_3$ is H, $NHCH_2CH_2N(CH_3)_2$, $NHCH_2CH_2NC_4H_8$, azetidinyl, furfuryl, morpholinyl, piperidinyl, piperazinyl, pyrrolidinyl, tetrahydrofurfuryl, 2-methyl-1-aziridinyl, (dimethylamino)methyl-1-aziridinyl, 3-(dimethylamino)-1-azetidinyl, 3-hydroxy-1-pyrrolidinyl, 3,4-dihydroxy-1-pyrrolidinyl, or $NR_7R_8$, $OR_7$, $SR_7$, wherein $R_7$ and $R_8$ are independently alkenyl, alkynyl, alkoxy, alkylhalide, alkyldihalide, amine, cycloalkyl, carboxyalkyl, (acetylamino)alkyl, (dimethylamino)alkyl, 1-(methoxymethyl)alkyl, 2-(1,3-dioxolan-2-yl)alkyl, 4,4-dimethoxybutyl, [[(1,1-dimethylethoxy)carbonyl]amino]alkyl, [[(1,1-dimethylethoxy)carbonyl]alkylamino]alkyl, 1-(hydroxymethyl)alkyl, 1-(hydroxymethyl)-2-methylalkyl, 2-(hydroxymethyl)cycloalkyl, (diethylamino)alkyl, 2-(dimethylamino)-1-methylethyl, (ethylmethylamino)alkyl, [(2-fluoroethyl)methylamino]alkyl, [(2,2-difluoroethyl)methylamino]alkyl, [bis(2-hydroxyethyl)amino]alkyl, (dimethyloxidoamino)alkyl, (trimethylammonio)alkyl, (1-aziridinyl)alkyl, (1-aziridinylmethyl)alkyl, (1-azetidinyl) alkyl, (2-deoxy-D-glucos-2-yl), (6-deoxy-D-glucos-6-yl), (1H-imidazol-4-yl)alkyl, (1-methyl-1H-imidazol-4-yl)alkyl, (1-methyl-1H-imidazol-5-yl)alkyl, (4-morpholinyl)alkyl, (4-pyridinyl)alkyl, (1-piperidinyl)alkyl, (1-piperazinyl)alkyl, (1-pyrrolidinyl)alkyl, (1-ethyl-2-pyrrolidinyl)methyl, or 2-(N-methyl-pyrrolidin-2-yl)ethyl;

$R_4$ and $R_5$ are independently H, $C_{1-6}$ alkyl, $C_{3-8}$ cycloalkyl, $C(=O)C_{1-10}$ alkyl, $C(=O)(CH_2)_n$-aryl, $C(=O)(CH_2)_n$-cycloalkyl, alkoxy, alkylthiol or sulfate, wherein n=1-10; and, $R_6$ is O, $OC(=O)NH_2$, $OC(=O)C_{1-10}$ alkyl, $OSO_2OH$, $OC(=O)OSO_2OH$ and $OC(=O)NR_9R_{10}$ wherein $R_9$ and $R_{10}$ are independently H and $C_{1-10}$ alkyl.

3. A purified compound of claim 1, wherein:
$R_1$ and $R_2$ are independently $C(=O)C_{1-10}$ alkyl;
$R_3$ is $NHCH_2CH=CH_2$, $NHCH_2CH_2N(CH_3)_2$, or $NHCH_2CH_2NC_4H_8$;
$R_4$ and $R_5$ are H, $C_{1-6}$ alkyl, $C_{3-8}$ cycloalkyl, $C(=O)C_{1-10}$ alkyl, $C(=O)(CH_2)_n$-aryl, $C(=O)(CH_2)_n$-cycloalkyl, alkoxy, alkylthiol or sulfate, wherein n=1-10; and,
$R_6$ is O, $OC(=O)NH_2$, $OC(=O)C_{1-10}$ alkyl, $OSO_2OH$, $OC(=O)OSO_2OH$ and $OC(=O)NR_9R_{10}$ wherein $R_9$ and $R_{10}$ are independently H and $C_{1-10}$ alkyl.

4. A purified compound of claim 1, wherein:
$R_1$ and $R_2$ are independently $SO_2OR_{10}$ wherein $R_{10}$ is H or $C_{1-10}$ alkyl.
$R_3$ is $NHCH_2CH=CH_2$, $NHCH_2CH_2N(CH_3)_2$, or $NHCH_2CH_2NC_4H_8$;
$R_4$ and $R_5$ are H, $C_{1-6}$ alkyl, $C_{3-8}$ cycloalkyl, $C(=O)C_{1-10}$ alkyl, $C(=O)(CH_2)_n$-aryl, $C(=O)(CH_2)_n$-cycloalkyl, alkoxy, alkylthiol or sulfate, wherein n=1-10; and,
$R_6$ is O, $OC(=O)NH_2$, $OC(=O)C_{1-10}$ alkyl, $OSO_2OH$, $OC(=O)OSO_2OH$ and $OC(=O)NR_9R_{10}$ wherein $R_9$ and $R_{10}$ are independently H and $C_{1-10}$ alkyl.

5. A pharmaceutical composition containing at least one of the purified compounds of claim 1 and a metal chelating agent.

6. A pharmaceutical composition containing at least one of the purified compounds of claim 2 and a metal chelating agent.

7. The pharmaceutical composition of claim 5 where in the metal chelating agent is a copper chelating agent.

8. The pharmaceutical composition of claim 5 where in the metal chelating agent is D-penicillamine.

9. A pharmaceutical composition comprising at least one of the compounds of claim 1 and at least one pharmaceutically-acceptable carrier.

10. A purified compound having the chemical structure:

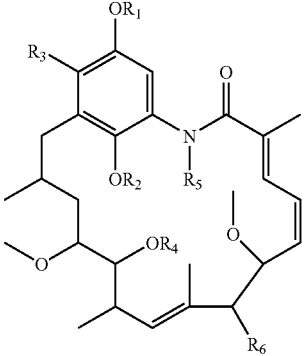

or a pharmaceutically-acceptable salt thereof; wherein:

$R_1$ and $R_2$ are independently $C_{1-6}$ alkyl, $C_{3-8}$ cycloalkyl, $C(=O)C_{1-10}$ alkyl, $C(=O)(CH_2)_n$-cycloalkyl, $C(=O)(CH_2)_n$-aryl, wherein n=1-10, alkoxy, alkylthiol, glycoside, glucuronide or sulfate, C(=O)CH(X)NH$_2$, and C(=O)CH(X)OH wherein X=an amino acid side chain;

R$_3$ is H, NHCH$_2$CH=CH$_2$, NHCH$_2$CH$_2$N(CH$_3$)$_2$, NHCH$_2$CH$_2$NC$_4$H$_8$, azetidinyl, furfuryl, morpholinyl, piperidinyl, piperazinyl, pyrrolidinyl, tetrahydrofurfuryl, 2-methyl-1-aziridinyl, (dimethylamino)methyl-1-aziridinyl, 3-(dimethylamino)-1-azetidinyl, 3-hydroxy-1-pyrrolidinyl, 3,4-dihydroxy-1-pyrrolidinyl, or NR$_7$R$_8$, SR$_7$, wherein R$_7$ and R$_8$ are independently H, alkenyl, alkynyl, alkoxy, alkylhalide, alkyldihalide, amine, cycloalkyl, carboxyalkyl, (acetylamino)alkyl, (dimethylamino)alkyl, 1-(methoxymethyl)alkyl, 2-(1,3-dioxolan-2-yl)alkyl, 4,4-dimethoxybutyl, [[(1,1-dimethylethoxy)carbonyl]amino]alkyl, [[(1,1-dimethylethoxy)carbonyl]alkylamino]alkyl, 1-(hydroxymethyl)alkyl, 1-(hydroxymethyl)-2-methylalkyl, 2-(hydroxymethyl)cycloalkyl, (diethylamino)alkyl, 2-(dimethylamino)-1-methylethyl, (ethylmethylamino)alkyl, [(2-fluoroethyl)methylamino]alkyl, [(2,2-difluoroethyl)methylamino]alkyl, [bis(2-hydroxyethyl)amino]alkyl, (dimethyloxidoamino)alkyl, (trimethylammonio)alkyl, (1-aziridinyl)alkyl, (1-aziridinylmethyl)alkyl, (1-azetidinyl)alkyl, (2-deoxy-D-glucos-2-yl), (6-deoxy-D-glucos-6-yl), (1H-imidazol-4-yl)alkyl, (1-methyl-1H-imidazol-4-yl)alkyl, (1-methyl-1H-imidazol-5-yl)alkyl, (4-morpholinyl)alkyl, (4-pyridinyl)alkyl, (1-piperidinyl)alkyl, (1-piperazinyl)alkyl, (1-pyrrolidinyl)alkyl, (1-ethyl-2-pyrrolidinyl)methyl, or 2-(N-methyl-pyrrolidin-2-yl)ethyl; and wherein when R$_1$ and R$_2$ are both H, R$_3$ is not NH$_2$;

R$_4$ and R$_5$ are independently H, C$_{1-6}$ alkyl, C$_{3-8}$ cycloalkyl, C(=O)C$_{1-10}$ alkyl, C(=O)(CH$_2$)$_n$-aryl, C(=O)(CH$_2$)$_n$-cycloalkyl, alkoxy, alkylthiol or sulfate, wherein n=1-10; and, R$_6$ is O, OC(=O)NH$_2$, OC(=O)C$_{1-10}$ alkyl, OSO$_2$OH, OC(=O)OSO$_2$OH and OC(=O)NR$_9$R$_{10}$ wherein R$_9$ and R$_{10}$ are independently H and C$_{1-10}$ alkyl.

* * * * *

UNITED STATES PATENT AND TRADEMARK OFFICE
CERTIFICATE OF CORRECTION

PATENT NO. : 7,608,611 B2
APPLICATION NO. : 11/218320
DATED : October 27, 2009
INVENTOR(S) : Ross et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 318 days.

Signed and Sealed this

Twelfth Day of October, 2010

David J. Kappos
*Director of the United States Patent and Trademark Office*